(12) United States Patent
Salih et al.

(10) Patent No.: US 9,333,212 B2
(45) Date of Patent: May 10, 2016

(54) PROTEASOME INHIBITORS AS OVOPROTECTIVE AGENTS TO SHIELD THE OVARY FROM CHEMOTHERAPY TOXICITY

(71) Applicant: Wisconsin Alumni Research Foundation, Madison, WI (US)

(72) Inventors: Sana M. Salih, Madison, WI (US); Elon Christiane Roti Roti, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 299 days.

(21) Appl. No.: 14/190,550

(22) Filed: Feb. 26, 2014

(65) Prior Publication Data

US 2014/0315859 A1   Oct. 23, 2014

Related U.S. Application Data

(60) Provisional application No. 61/775,127, filed on Mar. 8, 2013.

(51) Int. Cl.
*A61K 31/69* (2006.01)
*A61K 38/06* (2006.01)

(52) U.S. Cl.
CPC .................. *A61K 31/69* (2013.01); *A61K 38/06* (2013.01)

(58) Field of Classification Search
CPC ............................... A61K 31/69; A61K 38/05
USPC .......................................................... 514/64
See application file for complete search history.

(56) References Cited

PUBLICATIONS

Adams, J., Kauffman, M.; Development of the proteasome inhihitor Veleade((TM)) (Bortezomib). Cancer Investigation 2004; vol. 22: 304-311.
Bae, J., Leo, C.P., et al.; MCL-1S, a splicing variant of the antiapoptotic BCL-2 family member MCL-1, encodes a proapoptotic protein possessing only the BH3 domain. Journal of Biological Chemistry 2000; vol. 275: 25255-25261.
Brooks, A.D., Ramirez, T., et al.; The proteasome inhibitor bortezomib (Velcade) sensitizes some human tumor cells to Apo2L/TRAIL-mediated apoptosis. In: ElDeiry WS (ed.) Tumor Progression and Therapeutic Resistance, (2005) vol. 1059: 160-167.
Gatti, L., Benedetti, V., et al.; Synergistic interaction between the novel histone deacetylase inhibitor ST2782 and the proteasome inhibitor bortezomib in platinum-sensitive and resistant ovarian carcinoma cells. Journal of Inorganic Biochemistry 2012; vol. 113: 94-101.
Hartley, P.S., Bayne, R.A.L., et al.; Developmental changes in expression of myeloid cell leukemia-1 in human germ cells during oogenesis and early folliculogenesis. Journal of Clinical Endocrinology & Metabolism 2002; vol. 87: 3417-3427.
Hsu, S.Y., Hsueh, A.J.W.; Tissue-specific Bcl-2 protein partners in apoptosis: An ovarian paradigm. Physiological Reviews 2000; vol. 80: 593-614.

Hsu, S.Y., Kaipia, A., McGee, E., Lomeli, M., Hsueh, A.J.W.; Bok is a pro-apoptotic Bcl-2 protein with restricted expression in reproductive tissues and heterodimerizes with selective anti-apoptotic Bcl-2 family members. Proceedings of the National Academy of Sciences of the United States of America 1997; vol. 94: 12401-12406.
Hu, W., Zheng, R.R., et al.; Effects of bortezomib in sensitizing human prostate cancer cell lines to NK-mediated cytotoxicity. Asian Journal of Andrology 2012; vol. 14: 695-702.
Huang, C.M., Hu, X.X., Wang, L.B., Lu, S.Q., et al., Bortezomib suppresses the growth of leukemia cells with Notch1 overexpression in vivo and in vitro. Cancer Chemotherapy and Pharmacology 2012; vol. 70: 801-809.
Huang, H.B., Liu, N.N., Yang, C.S., et al.; HDAC Inhibitor L-Carnitine and Proteasome Inhibitor Bortezomib Synergistically Exert Anti-Tumor Activity In Vitro and In Vivo. Plos One 2012; vol. 7.
Jung, H.J., Chen, Z., McCarty, N.; Synergistic anticancer effects of arsenic trioxide with bortezomib in mantle cell lymphoma. American Journal of Hematology 2012; vol. 87: 1057-1064.
Kim, S.Y., Cordeiro, M.N., et al.; Rescue of platinum-damaged oocytes from programmed cell death through inactivation of the p53 family signaling network. Cell Death and Differentiation (2013) vol. 20: 987-997.
Kiyomiya, K., Matsuo, S., Kurebe, M.; Proteasome is a carrier to translocate doxorubicin from cytoplasm into nucleus. Life Sciences 1998; vol. 62:1853-1860.
Kiyomiya, K., Matsuo, S., Kurebe, M.; In situ photoaffinity labeling of proteasome with photoactive adriamycin analogue. Biochemical and Biophysical Research Communications 2000; vol. 273:928-932.
Kiyomiya, K., Matsuo, S., Kurebe, M.; Mechanism of specific nuclear transport of adriamycin: The mode of nuclear translocation of adriamycin-proteasome complex. Cancer Research 2001; vol. 61: 2467-2471.
Lawasut, P., Chauhan, D., et al.; New Proteasome Inhibitors in Myeloma. Current Hematologic Malignancy Reports 2012; vol. 7: 258-266.
Leo, C.P., Hsu, S.Y., et al.; Characterization of the antiapoptotic Bcl-2 family member myeloid cell leukemia-1 (Mcl-1) and the stimulation of its message by gonadotropins in the rat ovary. Endocrinology 1999; vol. 140: 5469-5477.
Liu, L., Yang, C., Herzog, C., et al.; Proteasome inhibitors prevent cisplatin-induced mitochondrial release of apoptosis-inducing factor and markedly ameliorate cisplatin nephrotoxicity. Biochemical Pharmacology 2010; vol. 79:137-146.
Ludwig, H., Viterbo, L., Greil, R., et al.; Randomized Phase II Study of Bortezomib, Thalidomide, and Dexamethasone With or Without Cyclophosphamide as Induction Therapy in Previously Untreated Multiple Myeloma. Journal of Clinical Oncology 2013; vol. 31: 247-255.
Lyu, Y.L., Kerrigan, J.E., Lin, C.P., et al.; Topoisomerase II beta-Mediated DNA double-strand breaks: Implications in doxorubicin cardiotoxicity and prevention by dexrazoxane. Cancer Research 2007; vol. 67: 8839-8846.

(Continued)

*Primary Examiner* — Raymond Henley, III
(74) *Attorney, Agent, or Firm* — Quarles & Brady, LLP

(57) ABSTRACT

A method of reducing damage to the ovary of a subject receiving chemotherapy is described. The method comprises the step of administering to the subject an amount of a proteasome inhibitor effective to reduce damage to the subject's ovary within a therapeutic time window prior to administration of a chemotherapeutic agent.

21 Claims, 20 Drawing Sheets
(5 of 20 Drawing Sheet(s) Filed in Color)

(56) References Cited

PUBLICATIONS

Matta, H., Chaudhary, P.M.; The proteasome inhibitor bortezomib (PS-341) inhibits growth and induces apoptosis in primary effusion lymphoma cells. Cancer Biology & Therapy 2005; vol. 4: 77-82.

Mizuno, H., Nakayama, T., et al.; Mast cells promote the growth of Hodgkin's lymphoma cell tumor by modifying the tumor microenvironment that can be perturbed by bortezomib. Leukemia 2012; vol. 26: 2269-2276.

Park, D.J., Lenz, H.J.; The role of proteasome inhibitors in solid tumors. Annals of Medicine 2004; vol. 36:296-303.

Richardson, P.G., Barlogie, B., et al. A phase 2 study of bortezomib in relapsed, refractory myeloma. New England Journal of Medicine 2003; vol. 348: 2609-2617.

Roti Roti, E.C., Leisman, S.K., Abbott, D.H., Salih, S.M.; Acute Doxorubicin Insult in the Mouse Ovary Is Cell- and Follicle-Type Dependent. Plos One 2012; vol. 7.

Yerlikaya, A., Okur, E., Ulukaya, E.; The p53-independent induction of apoptosis in breast cancer cells in response to proteasome inhibitor bortezomib. Tumor Biology 2012; vol. 33:1385-1392.

Zelinski M.B., et al. (2011) In vivo delivery of FTY720 prevents radiation-induced ovarian failure and infertility in adult female non-human primates. Fertility and Sterility vol. 95: 1440-U1289.

Roti Roti, E.C., Abbott, D.H., and Salih, S.M.; Proteasome Inhibitors Prevent Acute DXR Insult and Follicular Demise in the Mouse Ovary. 46th Annual Society of Study of Reproduction Meeting, Jul. 22-23, 2013 Montreal, Quebec Canada (poster presentation).

Figure 1 A-B

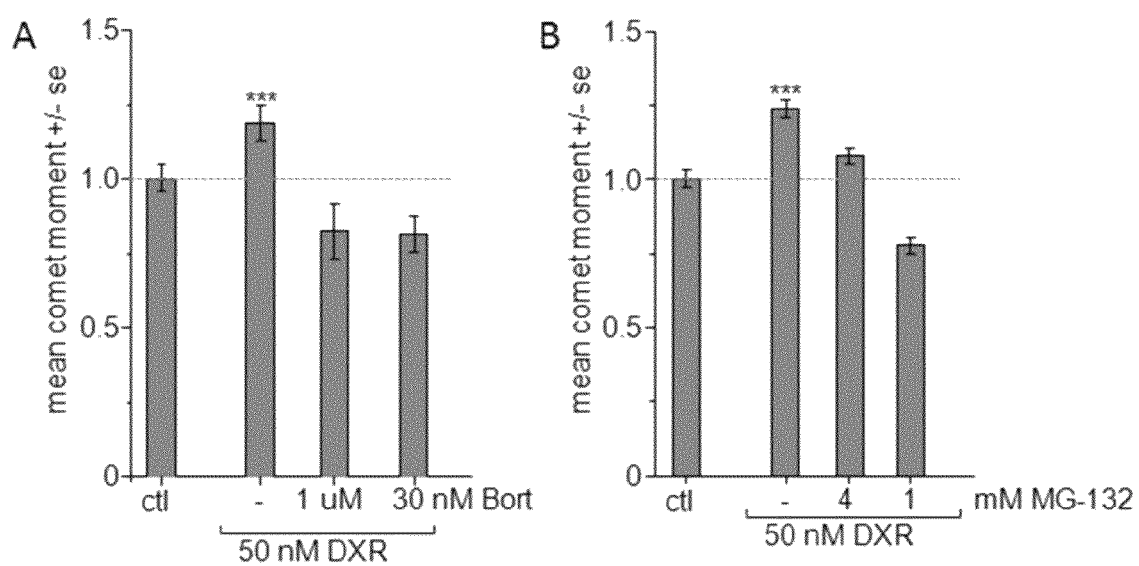
Figure 6 A-B

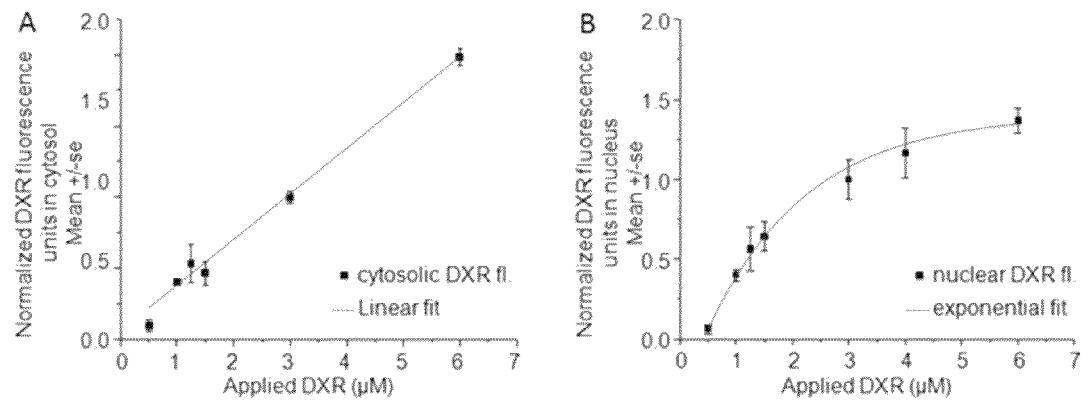
Figure 7 A-B

PROTEASOME INHIBITORS AS OVOPROTECTIVE AGENTS TO SHIELD THE OVARY FROM CHEMOTHERAPY TOXICITY

CROSS-REFERENCE TO RELATED APPLICATION

This application claims the benefit of U.S. Provisional Patent Application Ser. No. 61/775,127 filed on Mar. 8, 2013, herein incorporated by reference in its entirety.

STATEMENT REGARDING FEDERALLY SPONSORED RESEARCH OR DEVELOPMENT

This invention was made with government support under HD055894 awarded by the National Institutes of Health. The government has certain rights in the invention.

BACKGROUND OF THE INVENTION

Chemotherapy-induced primary ovarian insufficiency is an imminent health concern. Progressing female cancer survivorship demands new approaches to prevent unintended chemotherapy-induced primary ovarian insufficiency (POI) and subsequent early menopause. Premature menopause increases a woman's risk for complications due to estrogen depletion including osteoporosis, mental health disorders, and cardiovascular disease. By the year 2020, it is estimated that 1 in 500 adult women will be survivors of childhood cancer, over 8% of whom will experience POI.

The only available prophylactic fertility preservation therapy for prepubertal cancer patients who become cancer survivors requires surgically removing and freezing ovarian tissue prior to gonadotoxic cancer treatment for future re-transplantation. While the transplanted tissue provides fertility and natural hormonal cycling for a limited time, the procedure is expensive, invasive, considered experimental, and carries the risk of reintroducing the original cancer [1-5].

POI occurs more frequently in adult cancer patients, with up to 40% of breast cancer survivors suffering from the disorder [6-8]. Fertility preservation options for reproductively-mature female cancer patients include oocyte and embryo cryopreservation, but the requisite hormone treatments are contraindicated for patients with estrogen-responsive tumors, may delay cancer treatment, and do not preserve endocrine function. Oocyte and embryo cryopreservation are expensive procedures, have a modest success rate, expose the patient to considerable medical risks, and do not preserve overall endocrine health (normal hormonal regulation) nor prevent premature menopause.

Doxorubicin (DXR) Ovarian Toxicity.

DXR is an anthracyline used to treat roughly 50% of all cancer cases [9-11], and is associated with POI. Cancer therapies that typically utilize DXR generally have higher survival rates than others, but there are no clinical therapeutics to prevent DXR-induced POI; it is therefore these future survivors who will benefit from the drug-based ovarian shield proposed here. DXR can cause cell death via two distinct mechanisms; (1) intercalating into DNA and thus preventing resealing of topoisomerase II (topoII)-dependent double-strand DNA (dsDNA) breaks, and (2) inducing oxidative stress [12-18]. TopoII-dependent dsDNA damage appears to be the mechanism of DXR insult in ovarian cells [19] and requires drug transport into the cell nucleus where intercalation occurs.

Previous studies have shown DXR treatment induces a bi-temporal response in the mouse ovary with follicular apoptosis by 12 hours (hrs) post-injection [20, 21], followed by a return to 50% pre-DXR ovulation rate at 1 month post-DXR [21], and long-term follicular depletion [22, 23]. Oocytes exposed to DXR in vitro can undergo oxidative stress [20, 24-29] and exhibit chromosome condensation [30, 31].

To generate an in vivo model for testing putative ovoprotective agents, we previously characterized temporal and spatial accumulation of DXR in the mouse ovary, DXR-induced DNA damage, and consequent apoptosis [32]. These data demonstrate that DXR insult in the ovary is complex, involving responses that are cell- and follicle-type specific. DXR accumulates first in stromal cells, quantifiable by confocal microscopy at 2 hrs post-injection, then continuously shifts distribution to accumulate in follicles. Direct DXR-induced DNA damage prior to apoptosis was quantified using the neutral comet assay (NCA) in ovarian cells isolated from DXR-treated mice. This sensitive, single-cell electrophoretic assay reveals DNA damage in stromal/theca cells earlier than granulosa cells (2 hrs vs. 4 hrs post-injection, respectively).

As the first site of DXR-induced DNA damage, protecting stromal cells from chemotherapy insult may be critical to shielding the ovary as a whole. Stromal cells provide structural support for the ovary and determine the extracellular matrix composition, which in turn influences follicular maturation. Granulosa cells appear more sensitive to DXR-induced DNA damage, however, with an approximate 2-fold increase over control compared to a maximal 50% increase in stromal cells. It is therefore equally important to shield the granulosa cells, which maintain follicular health and nourish the oocyte, from chemotherapy.

Oocytes did not exhibit a significant increase in DNA damage over control until 10-12 hrs post-injection, a comparatively late sequel to granulosa cell damage occurring only after significant TUNEL signal in the granulosa cells indicates late-stage apoptosis and failing follicles. By 8 hrs post-DXR, antral follicles exhibit a 100% apoptotic index, and by 12 hours, secondary follicles plateau at 40% and primary follicles reach a 12% apoptotic index. These data suggest oocytes are either late targets of DXR or fail subsequent to follicular deterioration. Apoptotic events in primordial follicles (PFs) are not detected until 48 hrs post-DXR, despite significant DXR accumulation. The PFs are the follicle population which constitute the ovarian reserve and thus determine long-term fertility. PFs do sustain DXR-induced DNA damage, —as indicated by the appearance of phosphorylated γH2AX foci, the earliest cellular marker of dsDNA breaks, 48 hrs post-DXR. The complex ovarian response to DXR indicates that a successful ovarian protective agent needs to protect each ovarian cell type, as well as follicles at multiple stages.

Proteasome Inhibitors as Putative Ovoprotective Agents.

Though permeant to the cell plasma membrane, DXR is co-translocated across the nuclear membrane with the proteasome [33, 34], providing a potential mechanism to intercept nuclear DXR accumulation. The proteasome itself is responsible for over 90% of cellular protein turnover [35]. To regulate nuclear protein turnover, the assembled, active proteasome complex is translocated from the cytosol to the nucleus based in part on nuclear localization signals [36]. The proteasome is not structured like traditional transporters nor is the physiologic function drug transport, but the proteasome does mediate DXR nuclear accumulation [33, 37, 38]. Inhibitors including MG-132 and bortezomib (Bort), an aldehyde and boronate peptide, respectively, bind the proteasome active site with high affinity and specificity. Both MG-132 and Bort prevent DXR nuclear accumulation in L1210 cells by competing with DXR for binding to the proteasome active site [33]. MG-132 also prevents DXR-induced DNA damage in cardiac-derived H9C2 cells [39].

Well-tolerated in normal tissue, Bort is already approved for clinical use in anti-cancer therapies. Bort sensitizes myelomas and lung cancers to traditional chemotherapy, and is being tested to treat a variety of other cancers [40-107]. The toxicity in cancer cells is due to their requirement for rapid NF-κB turnover mediated by the proteasome to facilitate DNA transcription and rapid cell division [108-110].

Proteasome Inhibitor-mediated Ovoprotective Shielding Across Chemotherapy Drug Classes.

A further challenge facing the field of oncofertility is to avoid a scenario in which patients require an ovoprotective agent to correspond to each drug in their chemotherapy cocktail. The first member of the platinum-containing anti-cancer drugs, cisplatin is another common chemotherapy agent associated with high risk for POI [111]. Platinum drugs bind DNA and induce crosslinking which ultimately leads to apoptosis. Cisplatin is used in combination with DXR to treat hepatoblastoma (childhood liver cancer), neuroblastomas, osteosarcomas, Ewing and soft tissue sarcomas, endometrial cancer, and some triple negative breast cancers. In the rodent ovary, a single dose of cisplatin causes primordial follicle and oocyte destruction, decreases pregnancy rates and pups per litter in mice, and decreases circulating and follicular levels of anti-mullerian hormone (AMH) in rats [112-116]. Circulating AMH levels correlate with ovarian reserve such that a decrease in AMH is an indicator of POI. Also toxic to other organs, cisplatin causes nephrotoxicity by inducing depletion of the antiapoptotic protein, Mcl-1, and subsequent mitochondrial release of AIF [117]. Bort shields the kidney from cisplatin toxicity by preserving Mcl-1 levels [117]. Mcl-1 plays a critical role in follicle turnover as well [118-122]. This suggests Bort may also effectively shield the ovary from the platinum drug, albeit via a different mechanism than DXR shielding: preventing cisplatin-induced Mcl-1 depletion.

There is a critical need to develop a drug-based ovarian shield given routinely at the time of chemotherapy treatment to preserve both fertility and ovarian estrogen in female cancer patients regardless of age and cancer type. The long-term health consequences of early menopause in cancer survivors are expensive, and can include fertility treatment (IVF), as well as life-long treatment for osteoporosis, heart disease, and mental disorders as a result of estrogen depletion. Drug-based chemoprotection has the potential to overcome current obstacles in oncofertility by preserving ovarian endocrine function in a cost-effective, easily administered, non-invasive manner and avoiding health complications associated with premature menopause.

SUMMARY OF THE INVENTION

In general, the present invention provides a method of reducing damage to the organ systems of a subject receiving chemotherapy. One exemplary organ that can be protected by the method is ovary. The method comprises the step of administering to the subject an amount of a proteasome inhibitor effective to reduce damage to the subject's ovary within a therapeutic time window prior to administration of a chemotherapeutic agent.

In one embodiment, the therapeutic time window is in the range of about 30 minutes to about 2 hours. Preferably, the time window is about 30 minutes, 45 minutes, one hour, 1.5 hours and two hours. More preferably, the time window is about one hour.

In one embodiment, the proteasome inhibitor is administered at a dose in the range of 3% to 99% of the dose of the proteasome inhibitor typically used in a chemotherapy regimen. Preferably, the dose is 33% of the dose typically used in a chemotherapy regimen.

In one embodiment, the proteasome inhibitor is administered in a dose in the range of about 0.04 mg/m$^2$ to about 1.0 mg/m$^2$. Preferably, the dose is about 0.43 mg/m$^2$.

In one embodiment, the proteasome inhibitor is selected from the group consisting of bortezomib, carfilzomib, marizomib, CEP-18770, MLN-9708. ONX-0912, MG-132, PR-171, peptide vinyl sulfone, peptide 2-keto-1,3,4-oxadiazole, NPI-0052, TMC-95A, CVT-650, 2-aminobezylstatine derivative, trimethol-L-phenylalanine tripeptide, thiostrepton, MG-162, and mixtures thereof. Preferably, the proteasome inhibitor is bortezomib or MG-132.

In one embodiment, the chemotherapeutic agent is selected from the group consisting of anthracyclines, platinum drugs, intercalating chemotherapeutic agents, topoisomerase poisons, cyclophosphamide drugs, and mixtures thereof.

In one related embodiment, the anthracycline is selected from the group consisting of Daunorubicin (Daunomycin), Daunorubicin (liposomal), Doxorubicin (Adriamycin), Doxorubicin (liposomal i.e. Doxil), Epirubicin, Idarubicin, Valrubicin, Mitoxantrone, and mixtures thereof. Preferably, the anthracycline is Doxorubicin.

In one related embodiment, the platinum drug is selected from the group consisting of Cisplatin, Carboplatin, Oxaliplatin, and mixtures thereof.

In one related embodiment, the intercalating chemotherapeutic agent is selected from the group consisting of dactinomycin, erlotinib, and mixtures thereof.

In one related embodiment, the topoisomerase poison is selected from the group consisting of etoposide (VP-16), teniposide, doxorubicin, daunorubicin, mitoxantrone, amsacrine, ellipticines, aurintricarboxylic acid, HU-331, irinotecan, topotecan, camptothecin, lamellarin D, and mixtures thereof.

In another related embodiment, the cyclophosphamide drug is selected from cyclophosphamide, alkylating chemotherapeutic agents, ifosfamide, melphalan, budulfan, uracil mustard, chlorambucil, and mixtures thereof.

BRIEF DESCRIPTION OF THE DRAWINGS

The patent or application file contains at least one drawing in color. Copies of this patent or patent application publication with color drawings will be provided by the Office upon request and payment of the necessary fee.

FIG. 6. Proteasome inhibitors Bortezomib and MG-132 both limited DXR-induced dsDNA breaks in KK-15 cells. (A) Pretreating KK-15 cells for 1 h with the indicated Bortezomib doses prevented dsDNA breaks caused by 3 hr, 50 nM DXR treatment, as measured by the NCA. (B) Pretreating KK-15 cells for 1 h with the indicated MG-132 doses similarly prevented DXR-induced dsDNA breaks. Bar graphs summarize comet moment data. Bortezomib (n=3, *$p<0.001$), MG-132, (n=4, *$p<0.001$) ANOVA with Bonferroni means comparison.

FIG. 7. Summary graphs describe linear accumulation of DXR in the cytosol (A), but non-linear accumulation in the nucleus (B). The fl. intensity units of these samples between wavelengths emission 597 and 601 were averaged to give the peak fl. signal for each treatment group and normalized to the 3 μM DXR treatment. Standard errors were pooled.

DESCRIPTION OF THE INVENTION

Figure 1:
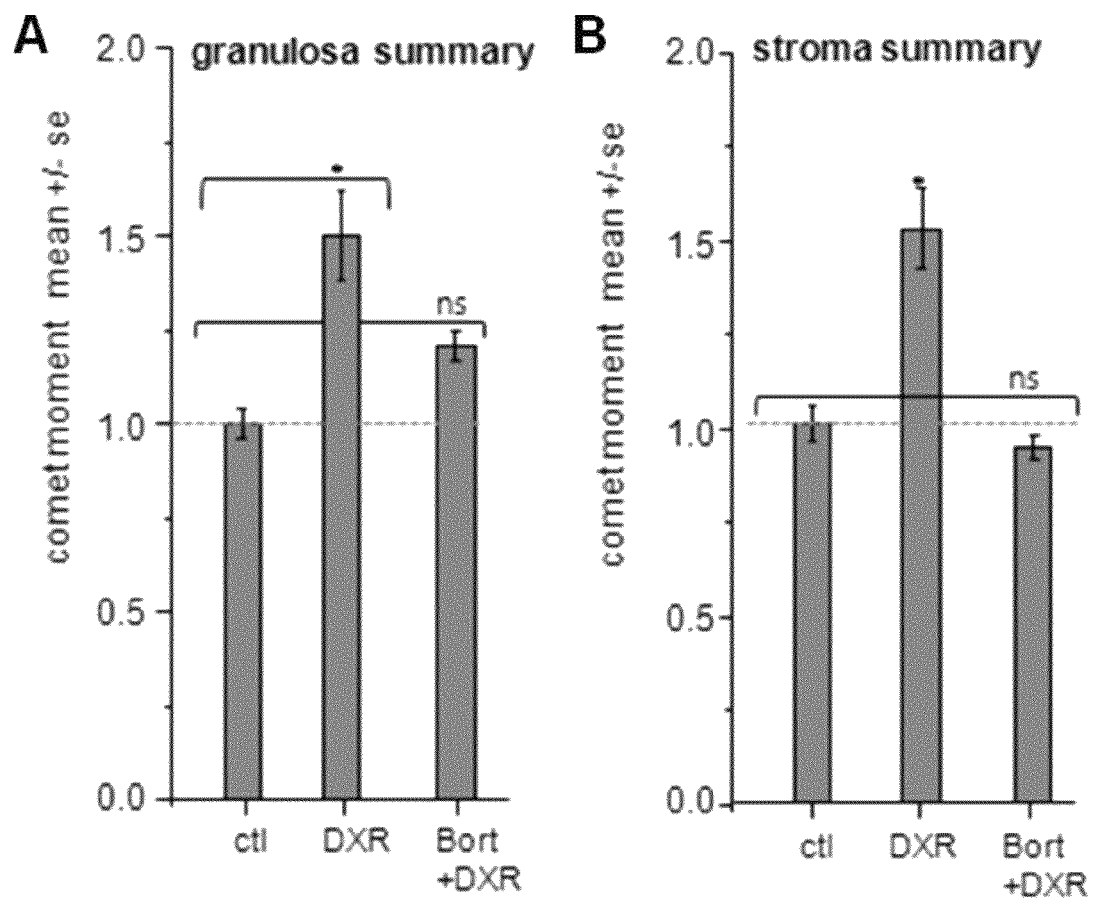
FIG. 1. Bort pretreatment attenuates DXR-induced DNA damage in mouse granulosa and stroma cells after in vivo treatment. Ovaries were harvested 12 hrs post-DXR injection and dsDNA breaks measured in single cell preparations. A) summary data of granulosa cell DNA damage B) summary data of stromal cell DNA damage. *p<0.05, n=4 mice.

The present inventors have surprisingly uncovered that proteasome inhibitors could bind the proteasome, blocking the chemotherapeutic agent transport into the nucleus of cells. Based on this discovery, the inventors envision that proteasome inhibitors may substantially reduce and even prevent ovarian damage caused by chemotherapeutic agents, thereby preserving ovarian function and protecting both the oocytes and supporting ovarian granulosa, theca, and stromal cells of a subject, regardless of the age of the subject and the type of cancer.

In general, the present invention provides a method for reducing damage to the ovary of a subject receiving chemotherapy. The method comprises the step of administering to the subject an effective amount of a proteasome inhibitor within a therapeutic time window prior to administration of a chemotherapeutic agent.

One of the most important advantages of the present invention is that it can reduce the chemotherapy damage to ovary, including all ovarian cells. Because the supporting cells of the ovary regulate the hormone environment critical to maintaining oocyte health as well as systemic hormone balance throughout the body, protecting all ovarian cells is critical to ovarian health, endocrine function, and overall fertility. While current cryopreservation technologies save oocytes, they do not preserve endocrine function of the ovary and therefore do not prevent premature menopause in female cancer survivors. Thus, the present invention not only can protect oocyte, but also can preserve endocrine function, preventing or delaying chemotherapy-induced primary ovarian insufficiency and subsequent menopause.

By "ovary", we mean an ovum-producing reproductive organ. The definition also includes ovarian follicles, which is the basic units of female reproductive biology. At the cellular level, the ovary contains all the cells of the ovary or any cells presented or found in the ovary. In one embodiment, the ovary includes the oocyte, hormone-producing cells, granulosa cells, theca, and stromal cells, as well as the cells of the internal and external theca layers and all associated vasculature.

By "reducing damage" or "reduction of damage", we mean a process which is capable of reducing, mitigating, and/or delaying chemotherapy-associated toxicities, so that the degree of safety of a subject's overall chemotherapeutic treatment is increased and adverse physiological responses to chemotherapeutic intervention is reduced. It may also reduce, prevent, mitigate, and/or delay the addition of, or the augmentation of medically-unacceptable adverse effects that may otherwise limit or interfere with the safety and utility of chemotherapy. The term "reducing damage" also means fully or at least partially preserving or recovering endocrine function, estrogen levels, anti-mullerian hormone (AMH) levels, and/or fertility in women exposed to chemotherapy, or reducing the risk of estrogen depletion and/or decreased fertility as the result of chemotherapy, such as the risk of temporary or permanent stop of egg production, temporary or permanent depletion/loss of estrogen production, temporary or permanent AMH depletion, the risk of miscarriage, the risk of premature birth, the risk of low birth weight or other problems.

"Damage" includes but is not limited to, direct DNA damage, oxidative stress, cellular demise (apoptosis/necrosis), reduced hormone production, and overall follicular depletion and decreased fertility caused by the adverse impact associated with chemotherapy.

In one embodiment, the reduction of the damage includes a process of preventing toxicities caused by the chemotherapeutic agent.

There are also some other benefits associated with the reduction of the damage. The action of proteasome inhibitors should similarly protect all other healthy organ systems in the body because the proteasome inhibitor is highly conserved across cells and organs, particularly those comprised of slowly- or non-dividing cells. Therefore proteasome inhibitor administration should improve patient tolerance of the chemotherapeutic agent. For example, the reduction may allow physicians to administer increased dose levels of chemotherapeutic agents; allow administration of chemotherapeutic agents more frequently, i.e., with shorter time intervals between treatment or actual treatment time; allow increases in the number of chemotherapy treatments by the prevention of cumulative toxicities; and/or allow reduced numbers of instances of dose modifications, treatment interruptions or delays, or discontinued treatments.

In one preferred embodiment, the reduction is a process of reducing, preventing, mitigating, and/or delaying chemotherapy-associated toxicities that have adverse effects on hormone-producing ovarian cells and oocytes, so that the risk to offspring is reduced and/or early menopause and the loss of fertility is prevented, minimized and/or delayed. The reduction may also reduce a risk of genetic defects in the oocyte and/or exposure of the embryo to chemotherapeutic agents.

By "proteasome inhibitors", we mean any substance which directly or indirectly inhibits the proteasome or the activity thereof. Exemplary proteasome inhibitors for use in the present invention include, without limitation, bortezomib, carfilzomib, marizomib, CEP-18770, MLN-9708. ONX-0912, MG-132, PR-171, peptide vinyl sulfone, peptide 2-keto-1,3,4-oxadiazole, NPI-0052, TMC-95A, CVT-650, 2-aminobezylstatine derivative, trimethol-L-phenylalanine tripeptide, thiostrepton, MG-162, and mixtures thereof.

In some embodiments, the proteasome inhibitor is bortezomib. Bortezomib can be obtained by any methods known in the art. For example, it is currently available in the clinic under the trade name VELCADE® (Millennium Pharmaceuticals) and is sold by a number of laboratory chemical suppliers under Bortezomib or PS-341, the original chemical name.

In some embodiments, the proteasome inhibitor is MG-132. MG-132 can be obtained by any methods known in the art. For example, it is currently available by laboratory chemical suppliers as a non-clinical grade drug.

The effective amount of a proteasome inhibitor to be administered for the purpose of this invention is important. By "effective amount", we mean an amount of a proteasome inhibitor sufficient to result in protection of gonads, follicles and/or oocytes against a damage caused by chemotherapeutic agents. The protection may be in the form of preventing damage or reducing the degree of damage. For proteasome inhibitors other than Bortezomib, it is anticipated the effective ovoprotective dose will be the dose that provides similar proteasome inhibition as that achieved by the specified Bortezomib dose range.

In some embodiments, the chemotherapeutic agent causes transient or permanent cessation of ovulation (e.g., amenorrhea), and administration of an effective amount of a proteasome inhibitor restores at least some of the ovulation.

In some embodiments, the chemotherapeutic agent increases the amount of oocytes having genetic defects, and administration of an effective amount of a proteasome inhibitor prevents or at least partially reverses the increase in oocytes with genetic defects.

In some embodiments, the chemotherapeutic agent causes damage to the gonads, follicles and/or oocytes, and administration of an effective amount of a proteasome inhibitor prevents or at least reduces this damage.

Obviously, the specific "effective amount of a proteasome inhibitor" will vary with such factors as the proteasome inhibitor, the formulations employed and delivered, the condition of the subject, the type of cancer being treated, the duration of the treatment, the nature of concurrent therapy, route of delivery, etc.

Preferably, the effective amount of a proteasome inhibitor in accordance with the present invention is in the range of 3% to 99% of the dose of the proteasome inhibitor typically used in a chemotherapy regimen. For example, the effective amount of a proteasome inhibitor is about 3%, 10%, 20%, 33%, 40%, 50%, 60%, 70%, 80%, or 99% of the dose of the proteasome inhibitor typically used in a chemotherapy regimen (the standard chemotherapy dose). More preferably, the effective amount of a proteasome inhibitor is about 33% of the dose typically used in a chemotherapy.

The standard chemotherapy dose of proteasome inhibitors typically used in chemotherapy is well-established in practice or may be determined by any method known in the art. For example, depending on the particular inhibitor used, the dose can be in the range of about 0.1 mg/m$^2$ to about 3 mg/m$^2$. One specific example of the standard chemotherapy dose is about 1.3 mg/m$^2$.

Accordingly, in some embodiments, the effective amount of a proteasome inhibitor in accordance with the present invention is in the range of about 0.04 mg/m$^2$ to about 1.0 mg/m$^2$. Preferably, the effective amount of a proteasome inhibitor is about 0.04, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, and 1.0 mg/m$^2$. More preferably, the effective amount of a proteasome inhibitor is about 0.43 mg/m$^2$, which is 33% of a typically used chemotherapy dose of 1.3 mg/m$^2$.

The term "about" as used herein means greater or lesser than the value or range of values stated by ⅕ of the stated values, but is not intended to limit any value or range of values to only this broader definition. For instance, a dose value of about 33% means a dose between 27% and 39%. Each value or range of values preceded by the term "about" is also intended to encompass the embodiment of the stated absolute value or range of values.

By "chemotherapy" and "chemotherapeutic", we mean a treatment or a serial treatments with a chemical agent capable of causing damage (e.g., cell death and/or DNA mutation) to proliferating cells, typically cancer cells. The chemotherapy may be a treatment for a malignant disease or disorder (e.g., cancer), but chemotherapy for other conditions (e.g., autoimmune diseases, or conditions that require bone marrow ablation) is also included.

Preferably, "chemotherapy" and "chemotherapeutic" refer to treatment with chemotherapeutic agents that cause damage to gonadal tissue (e.g., gonads and/or follicles) and/or oocytes, either as an adverse side effect or per se.

Chemotherapeutic agents in accordance with the present invention include, but not limited to, anthracyclines, platinum drugs, intercalating chemotherapeutic agents, topoisomerase poisons, cyclophosphamide drugs, and mixtures thereof. All these chemotherapeutic agents can be obtained by any method known in the art. For example, they may be commercially available.

In some embodiments, the chemotherapeutic agent is an anthracycline. Exemplary anthracyclines include, without limitation, Daunorubicin (Daunomycin), Daunorubicin (liposomal), Doxorubicin (Adriamycin), Doxorubicin (liposomal i.e. Doxil), Epirubicin, Idarubicin, Valrubicin, Mitoxantrone, and mixtures thereof. Preferably, the chemotherapeutic agent is Doxorubicin In some embodiments, the chemotherapeutic agent is a platinum drug. Exemplary platinum drugs include, without limitation, Cisplatin, Carboplatin, Oxaliplatin, and mixtures thereof.

In some embodiments, the chemotherapeutic agent is an intercalating chemotherapeutic agent. Exemplary intercalating chemotherapeutic agents include, without limitation, dactinomycin, erlotinib, and mixtures thereof.

In some embodiments, the chemotherapeutic agent is a topoisomerase poison. Exemplary topoisomerase poisons include, without limitation, etoposide (VP-16), teniposide, doxorubicin, daunorubicin, mitoxantrone, amsacrine, ellipticines, aurintricarboxylic acid, HU-331, irinotecan, topotecan, camptothecin, lamellarin D, and mixtures thereof.

In some embodiment, the chemotherapeutic agent is a cyclophosphamide drug. Cyclophosphamide belongs to the class of alkylating chemotherapy. Other members of this class include, without limitation, ifosfamide, melphalan, budulfan, uracil mustard, and chlorambucil.

The timing for administering the proteasome inhibitor is important. The proteasome inhibitor must be administered within a certain therapeutic time window prior to the administration of a chemotherapeutic agent. The time window is effective if it provides at least a period of time for the proteasome inhibitor to bind the proteasome and slow or even block the transport of the chemotherapeutic agent into nucleus and/or mitigate other mechanistic pathways for chemotherapy injury in the ovary, including specific protein turnover. Of course, the specific time window may vary, depending upon the chemotherapeutic agent and/or the proteasome inhibitor, the amount of the agent and/or the inhibitor being delivered, the formulations being employed and delivered, the route of delivery, the condition of the subject receiving the agent, the type of the cancer being treated, the duration of the treatment, the nature of concurrent therapy, etc. On the other hand, in a clinic setting, one would prefer the treatment to be conducted in an efficient manner for obvious practical reasons. For example, after receiving a proteasome treatment, one may prefer to wait for about 30 minutes to about 2 hours before he or she receives a chemotherapeutic treatment.

Thus, in some preferred embodiments, the time window between the administrations of a proteasome and a chemotherapeutic agent is between about 30 minutes to two hours. In some embodiments, the time window can be about 30 minutes, 45 minutes, one hour, 1.5 hours, or two hours. More preferably, the time window is about 30 minutes or one hour.

The administration of a proteasome inhibitor can be carried out by any protocols known in the art. The administration may vary depending on doses, dosage forms, formulations, compositions and/or administration devices involved. The form of the proteasome inhibitor may also contain a pharmaceutically-acceptable carrier thereof, and/or an analog thereof. For example, the proteasome inhibitor may be administered in forms for oral administration (for example by means of tablets, troches, lozenges, sublingual absorption, and the like), injection (for example: subcutaneous administration, intradermal administration, subdermal administration, intramuscular administration, depot administration, intravenous administration or intra-arterial administration, intra-cavitary administration (e.g., administration into the intrapleural or intraperitoneal space), and any other forms known in the art.

It should be understood that the present invention has been described above with respect to its preferred embodiments. Other forms of this concept are also intended to be within the scope of the claims.

EXAMPLES

Example 1

This Example is a preliminary test of whether clinically-approved bortezomib (Bort) protects the ovary from doxorubicin (DXR) insult. The neutral comet assay was used to measure acute DXR-induced double-strand DNA breaks in an in vivo mouse model as previously described [32]. 4-week-old adolescent female CD1 mice were pre-treated with intraperitoneal (i.p.) injection of 0.143 mg/kg Bort 1 hr prior to 20 mg/kg DXR.

Figure 2:
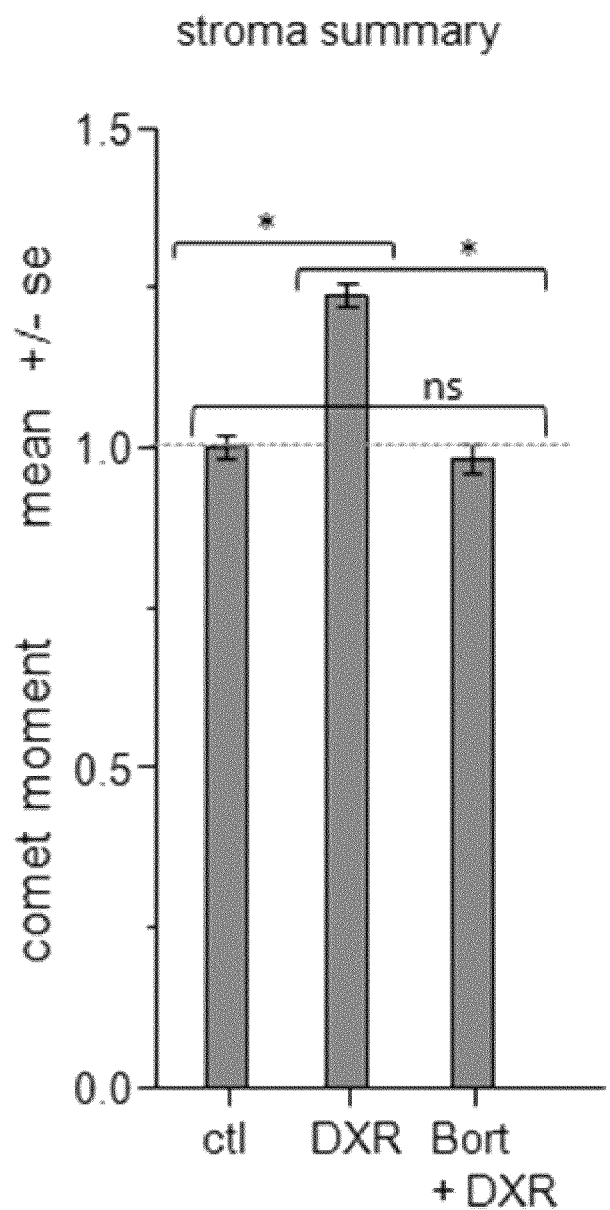
FIG. 2. Bort pretreatment attenuates DXR-induced DNA damage in mouse stroma cells 4 hrs after in vivo treatment. Ovaries were harvested 4 hrs post-DXR injection and dsDNA breaks measured in single cell preparations. Summary data of stromal cell DNA damage. *p<0.05, n=4 mice.
Figure 3:
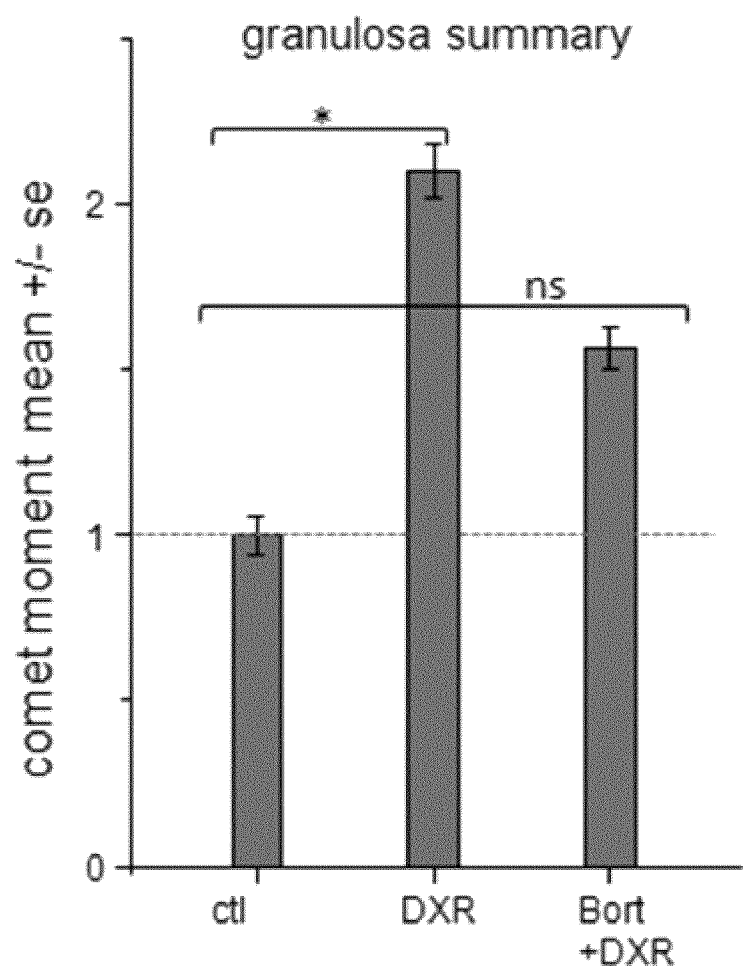
FIG. 3. Bort pretreatment attenuates DXR-induced DNA damage in mouse granulosa cells 24 hrs after in vivo treatment. Ovaries were harvested 24 hrs post-DXR injection and dsDNA breaks measured in single cell preparations. Summary data of granulosa cell DNA damage. *p<0.05, n=4 mice.

FIG. 1 shows that Bort attenuates DXR-induced DNA damage 12 hrs post-DXR in both granulosa and stromal cells. Similar Bort-mediated protection was observed 4 and 24 hrs post-injection (FIGS. 2 and 3, respectively). Further characterization of DXR-induced time-dependent DNA damage revealed that Bort pre-treatment prevented DXR-induced double strand DNA breaks in granulosa, stromal cells, and oocytes over the entire 24 hour acute insult period (FIG. 8).

Figure 4:
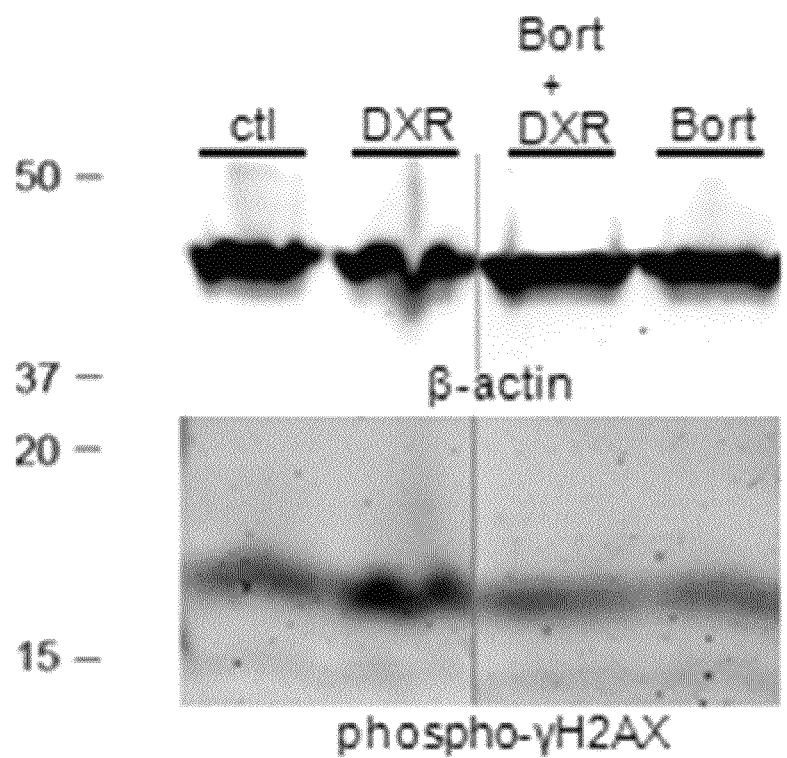
FIG. 4. Bort attenuates γH2AX phosphorylation in response to DXR in the mouse ovary. Western blot of ovarian lysates isolated 6 hrs post-DXR injection+/−1 hr Bort pretreatment is probed with antibodies recognizing β-actin and phosphorylated γH2AX as indicated.

Bort pretreatment also attenuated DXR-induced γH2A.X phosphorylation (activation), the earliest cellular response to dsDNA breaks. DXR increased γH2A.X phosphorylation, as demonstrated by an increase in intensity of the corresponding 17 kDa band on Western blots; this response was attenuated with Bort pretreatment (FIGS. 4 and 9).

Figure 5:
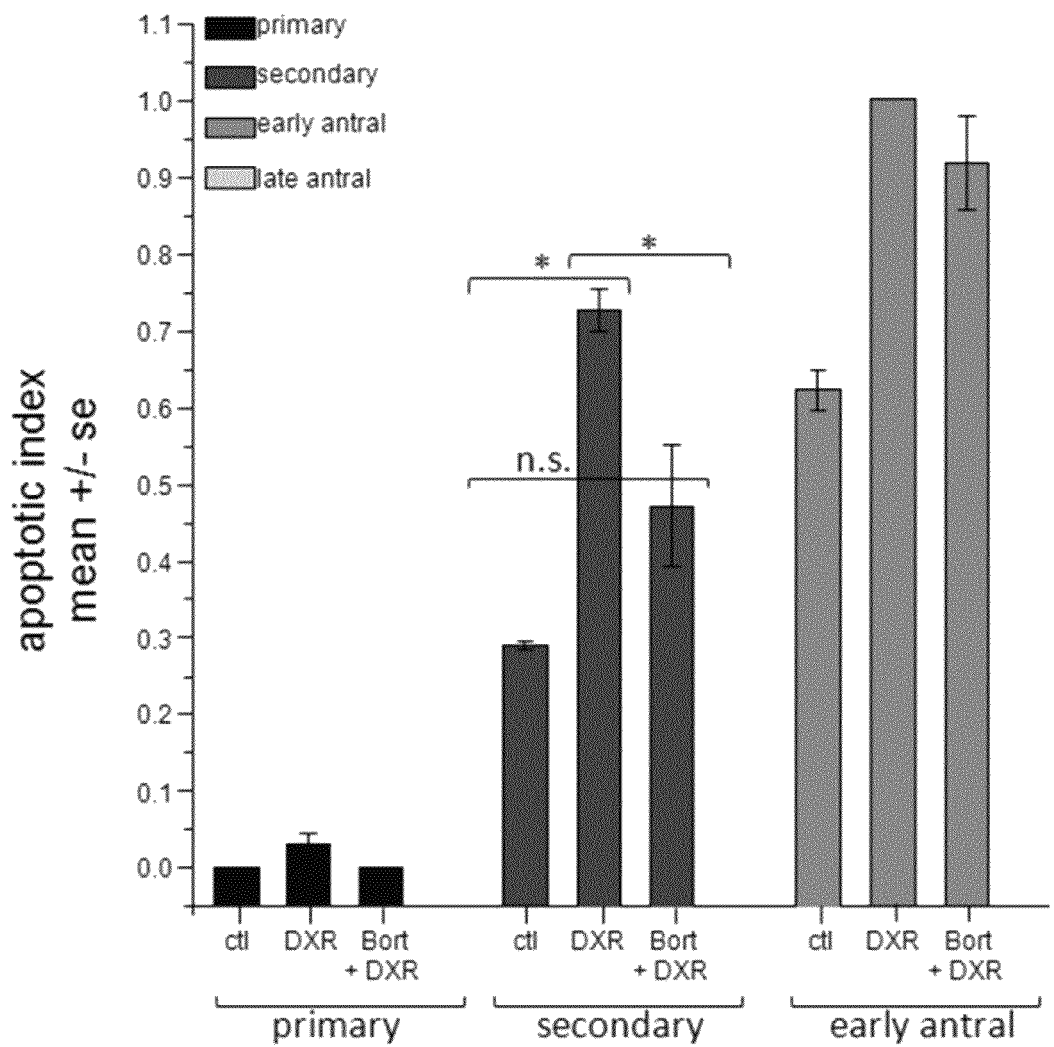
FIG. 5. Bort attenuates DXR-induced apoptosis in the mouse ovary. 4 week-old female CD-1 mice were injected i.p. with control saline+0.05% DMSO or 0.143 mg/kg Bort 1 hr prior to injection with 20 mg/kg DXR or saline. Ovaries were harvested from treated mice 12 hrs post-DXR injection, fixed, and processed for the TUNEL assay. Apoptotic index measures the fraction of cells dying via apoptosis in each group. *$p<0.05$ one-way ANOVA n=4 mice.
Figure 10A:
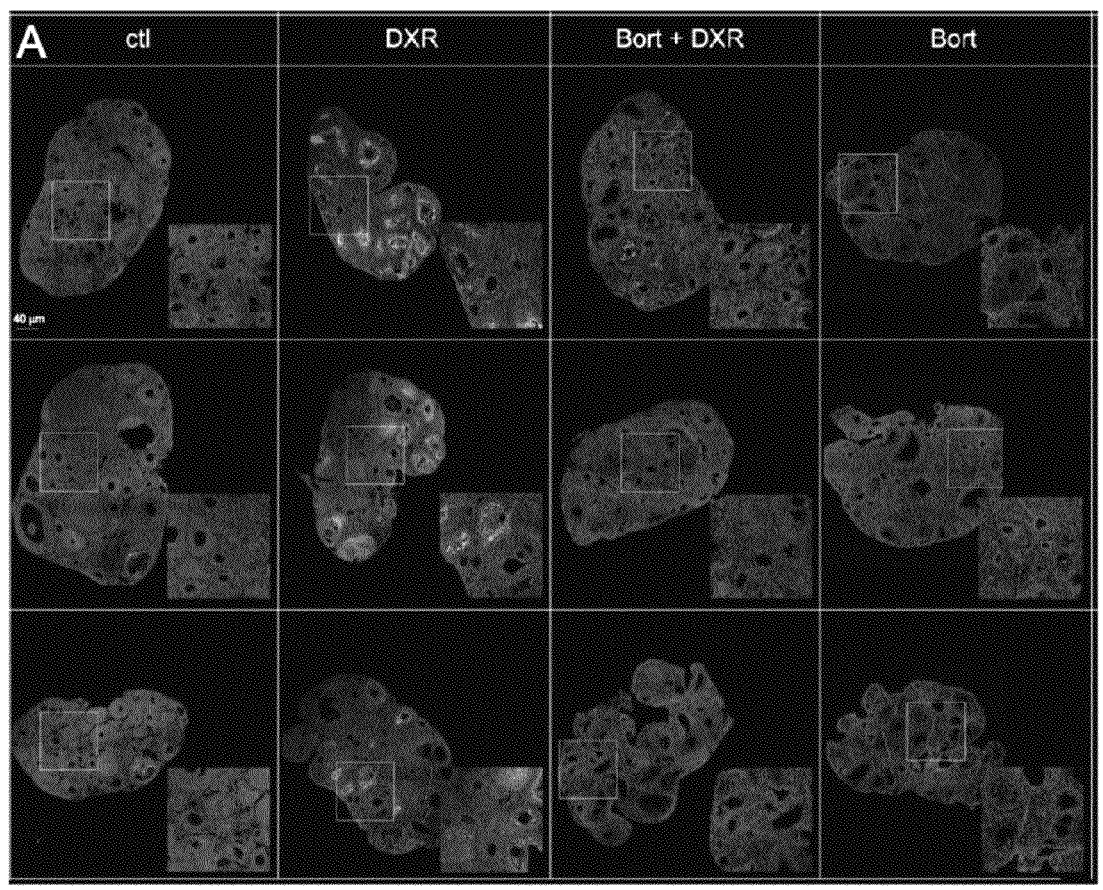
FIG. 10. Bort pretreatment prevented DXR-induced apoptosis in mouse ovarian follicles. A. Micrographs of mouse ovaries stained with TUNEL (green) or PI (red, nuclei), bar=40 μm). Representative images from 3 different mice are shown for each treatment condition. Insets are digital magnification. B. Bar graph quantifies the apoptotic index per follicle class calculated as fraction apoptotic/total follicles for each class. *$p<0.05$, one-way ANOVA, Bonferroni means comparison.
Figure 10B:
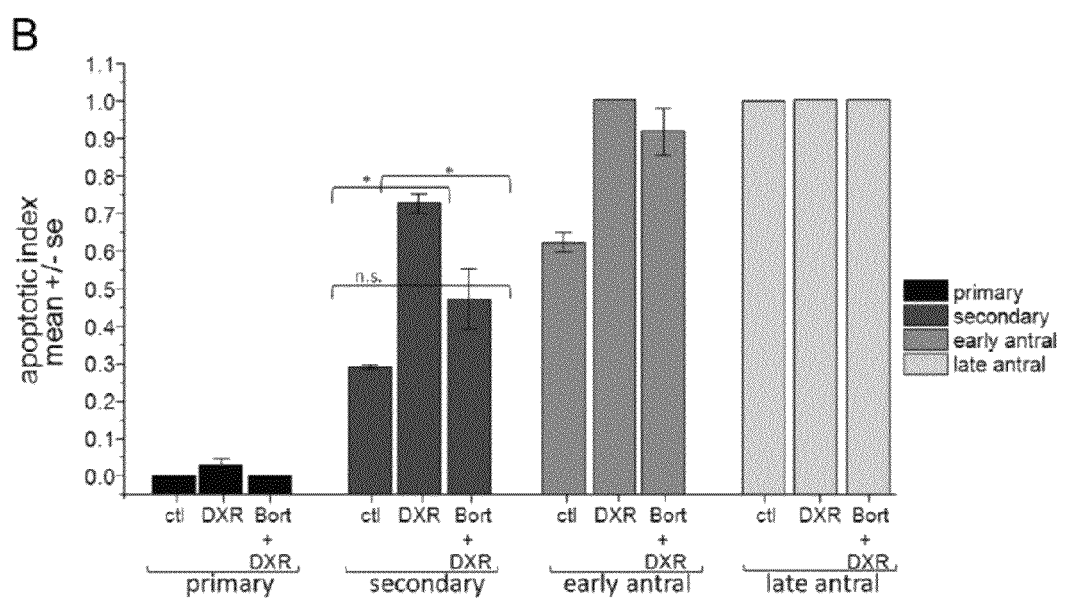

To determine whether Bort pretreatment prevents DXR-induced follicular apoptosis, ovaries were harvested from mice treated with control, DXR, or Bort+DXR, 12 hrs after chemotherapy administration. Ovaries were fixed and stained using the TUNEL assay [32]. Follicles were scored as apoptotic if they contained ≥4 TUNEL-positive granulosa cells [123]. While Bort did not prevent antral follicle apoptosis, pretreatment with the proteasome inhibitor significantly attenuated TUNEL signal in secondary follicles (FIGS. 5 and 10). Bort also appeared to decrease apoptosis in primary follicles, but the experiment will have to be repeated at longer time points, when higher percentages of primary follicles exhibit DXR-induced apoptosis to ascertain statistical significance. These data indicate Bort attenuates DXR-induced follicular demise in vivo.

To determine whether other catalytic proteasome inhibitors can also prevent DXR insult, we tested the hypothesis that a structurally unrelated proteasome inhibitor, MG-132, prevents DXR-induced DNA damage in immortalized KK-15 granulosa cells, a viable model for both DXR insult and protection [19]. KK-15 cells were pretreated with either Bort or MG-132, boronate and aldehyde inhibitors, respectively, for 1 hr prior to DXR. Both inhibitors prevented DNA damage induced by 50 nM DXR, the $LD_{50}$ for KK-15 cells (FIG. 6). These data demonstrate that structurally distinct catalytic proteasome inhibitors can similarly prevent DXR insult, consistent with a model in which the protection mechanism is competitive binding to the proteasome active site.

Quantifying the dose-dependence of DXR accumulation reveals facilitated transport into the nucleus in KK-15 cells, as expected for proteasome-mediated nuclear accumulation. DXR accumulation in cytosolic and nuclear cellular fractions was quantified based on DXR's autofluorescence from cells treated with varying concentrations of DXR. Briefly, cytosolic and nuclear fractions were treated with DNAse I to release bound DXR from the DNA [124]. The data in FIG. 7 demonstrate total DXR accumulation in the cytosol follows a linear fit (A, example from n=3), consistent with lipid-based diffusion. Nuclear accumulation, in contrast, is non-linear (B) and fits an exponential function, suggesting facilitated transport. These data are consistent with studies demonstrating proteasome-mediated translocation of DXR across the nuclear membrane [33, 37, 38].

Example 2

References cited in this Example are listed in the section of References as "References cited in the Example 2."

Methods

Chemicals. Bort was obtained from Simga, Complete protease inhibitors from Roche, DXR from the UW-Madison Chemo Pharmacy, and all other chemicals from Fisher.

Lysate Preparation and Western Blots. Ovaries were homogenized, protein quantified, and WBs were conducted previously described [9]. Blots were probed with rabbit anti-γH2AFX antibody (Abcam, 1:500), and mouse anti-β actin (Sigma, 1:10,000), rabbit anti-phospho AKT1 (Cell Signaling 1:1000), rabbit anti-PTEN (Cell Signaling 1:1000), and rabbit anti-Caspase 3 (Cell Signaling 1:1000. WBs were scanned and analyzed using the 5 LiCor Odyssey System (UW-Small Molecule Screening Facility) [9].

Mice. This study was conducted in accordance with the Guide for the Care and Use of Laboratory Animals and the Animal Welfare Act. Procedures were approved by the Medical School Animal Care and Use Committee of the University of Wisconsin (UW)-Madison. Animals were purchased through (Charles Rivers) and housed in the UW Animal Care Facility, accredited by the Association for Assessment and Accreditation of Laboratory Animal Care, and provided a standard care with free access to food and water. Four-week old female CD1 mice were treated with 0.143 mg/kg Bort or vehicle control, followed by 20 mg/kg DXR (twice the human equivalent dose) or saline via intraperitoneal injection (200 µL total volume/injection) 1 hour later. Three mice were injected per time point, 2, 4, 6, 12, and 24 hours, as indicated. Mice were euthanized with CO2 per approved protocol, and ovaries were processed as previously described [13].

Neutral Comet Assay. Ovaries were processed to provide enriched populations of granulosa cells/oocytes, and stromal/thecal cells that were utilized in the neutral comet assay [9, 13]. At least 100 granulosa and stromal cells and 50 oocytes were imaged from blinded slides per time point per mouse (3 mice/replicate) [9, 13]. The comet moment to quantify DNA damage was scored using CometScore software. Data were normalized to control for each experiment to allow pooling across experiments.

Fluorescence Microscopy. Images were collected using a Nikon A1 laser scanning microscope with a motorized stage to image the entire section at 400× magnification. Each spectral image was taken at the Z plane providing maximal signal in the section utilizing identical laser settings with the spectral scan head, exciting at 488 nm and collecting emissions from 520 nm through 720 nm at 10 nm intervals [13]. Images presented are overlays of all emissions, thereby including all signal over the DXR emission range. Total DXR fluorescence was measured in each section image using Nikon Elements, quantifying fluorescent intensity at each emission wavelength.

TUNEL Staining. Apoptosis was detected utilizing ApopTag Plus Fluorescein In Situ Apoptosis Detection Kit as previously described [13]. Nuclei were counterstained with 0.5 ug/mL Propidium Iodide. Apoptotic index was determined only counting follicles containing a visible oocyte; follicle types were differentiated by standard morphology and size ranges. Primary, secondary, and antral follicles were considered positive if they had ≥4 TUNEL-positive granulosa cells [23].

Statistics. Graphs and ANOVA analyses were generated using OriginLab. All one-way ANOVAs were conducted including means comparisons as indicated, set at p≤0.05.

Results and Discussion

We tested the hypothesis that Bort pretreatment prevents DXR-induced DNA damage utilizing the neutral comet assay to quantify dsDNA damage in all ovarian cell types over a 24-hr post-injection period. Four week-old adolescent mice were pretreated with 0.143 mg/kg Bort or vehicle control via i.p. injection 1 hour prior to 20 mg/kg DXR i.p. injection. The Bort dose corresponded to ⅓ the lowest human equivalent dose utilized in chemo regimens (0.43 mg/m2 vs. 1.3 mg/m2), while the DXR dose was double the standard human equivalent dose to allow direct imaging of DXR fluorescence in subsequent experiments.

Figure 8A:
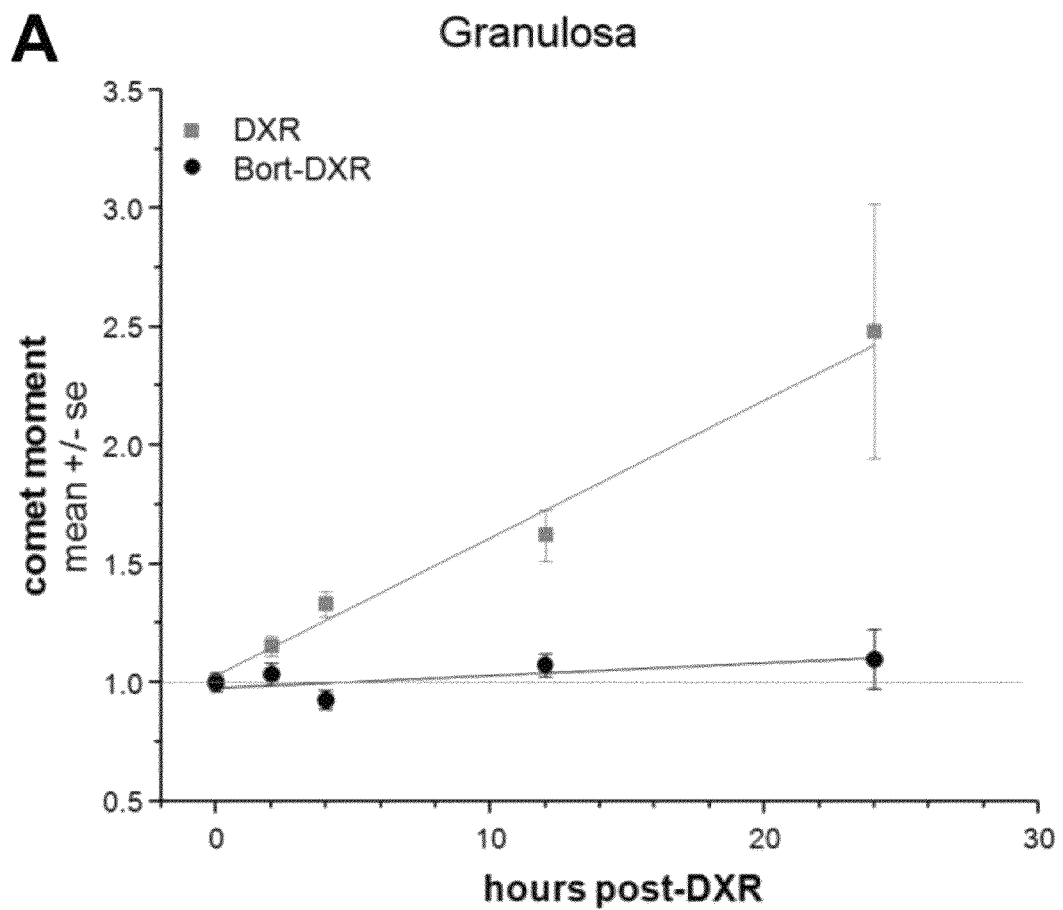
FIG. 8. Bort pretreatment prevents DXR-induced dsDNA breaks in ovarian cells. Summary data quantify dsDNA damage as the comet moment utilizing the comet assay. Trend lines included for visualization. Panels summarize DNA damage in granulosa cells (A.) and stromal cells (B.) as time post-DXR injection plotted against comet moment. DXR vs. Bort-DXR comet moment was significantly different at all time points for granulosa cells (A) and stromal cells (B), $p<0.05$, one-way ANOVA. (C.) Bar graph summarizes DNA damage in oocytes 24 hrs post-DXR injection. n=3 animals/group/time point/replicate, 4 replicates total. *$p<0.05$, one-way ANOVA.
Figure 8B:
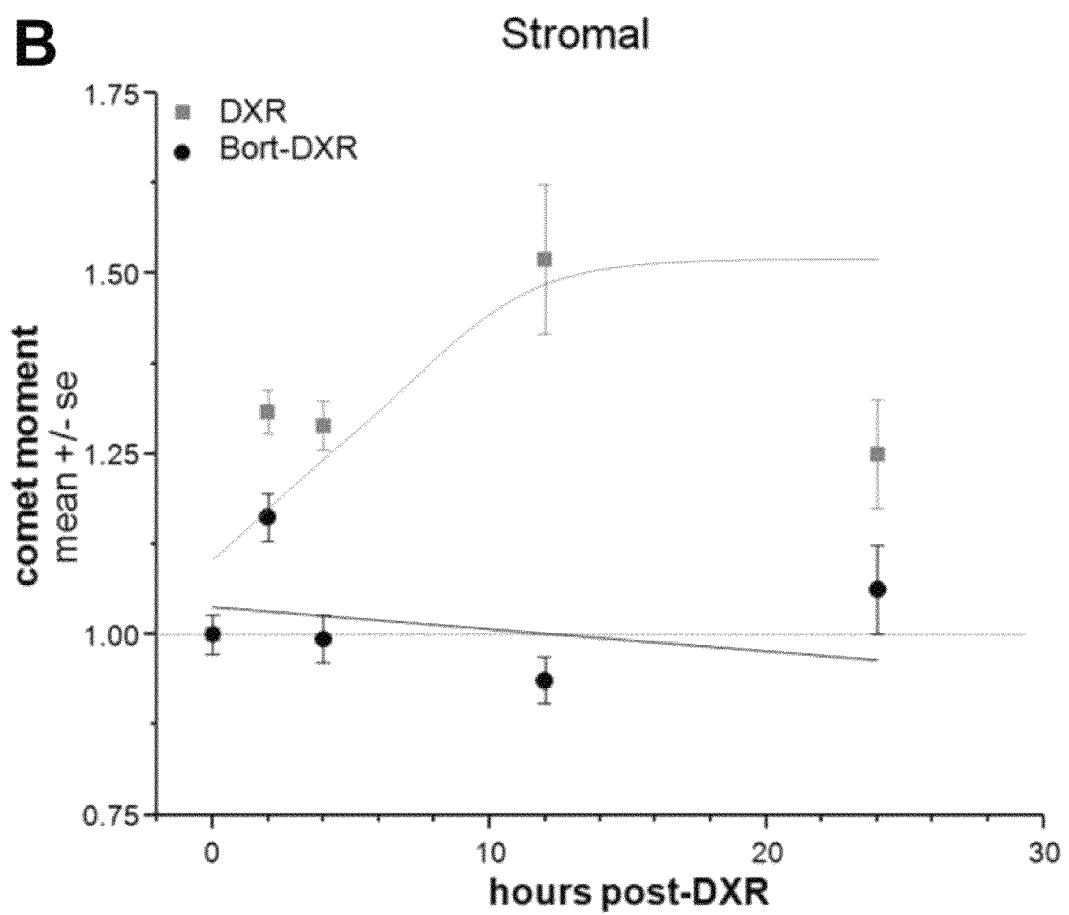
Figure 8C:
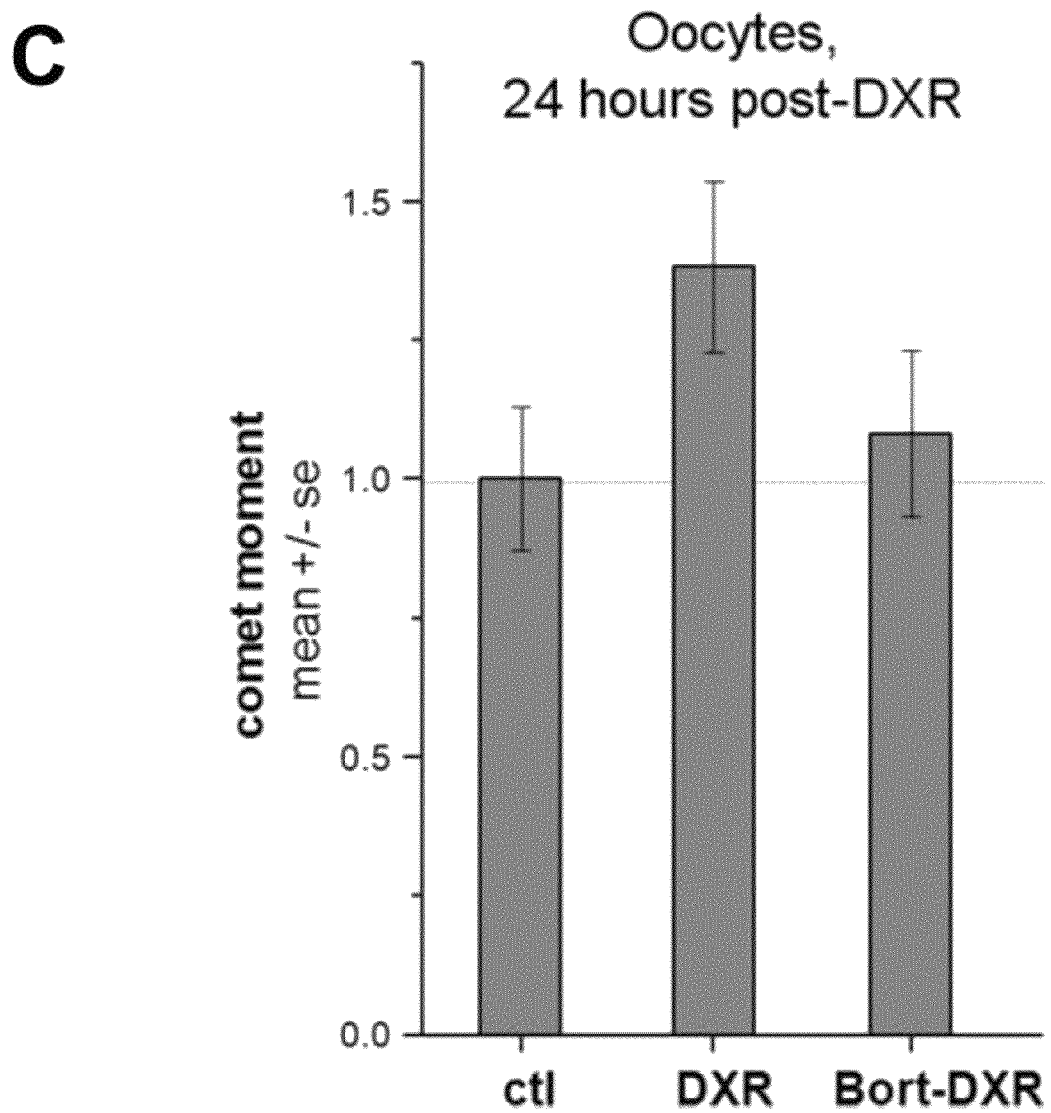

Quantifying dsDNA breaks as the comet moment in individual cells revealed that Bort prevented time-dependent DXR-induced DNA damage in granulosa and stromal/thecal cell-enriched populations in ovaries from treated mice 2 through 24 hrs post-injection (FIGS. 8a and 8b, respectively). Where the comet moment rose linearly to 250% control values following DXR treatment over time, Bort pretreatment maintained values within 10% of control in granulosa cells from Bort-DXR-treated mice (FIG. 8a). Similarly, DXR increased the comet moment in stromal cells to 150% control values, whereas Bort pretreatment maintained DNA damage within 16% of control (FIG. 8b). Not only was the initial onset of DNA damage blocked, but there was no delayed DNA damage response in the Bort-pretreated animals. DXR is rapidly cleared from the blood stream (within 15-30 minutes), and the lack of DNA damage over a 24-hr period suggests protection throughout the DXR clearance timeframe. These data indicate pretreatment with Bort provides protection across the entire acute DXR insult phase, rather than simply delaying DNA insult in the ovary. FIG. 8c demonstrates Bort also completely blocked DNA damage induced by DXR in oocytes at 24 hrs post-injection, manifest as a lack of increase in comet moment. Oocytes were not examined for DNA damage at earlier time points as our previous publication demonstrated oocytes do not exhibit DXR-induced DNA damage until at least 10 hrs post-injection. The comet assay therefore revealed Bort completely prevented DXR-induced DNA damage in all ovarian cell types over an acute 24-hr time period.

Figure 9A:
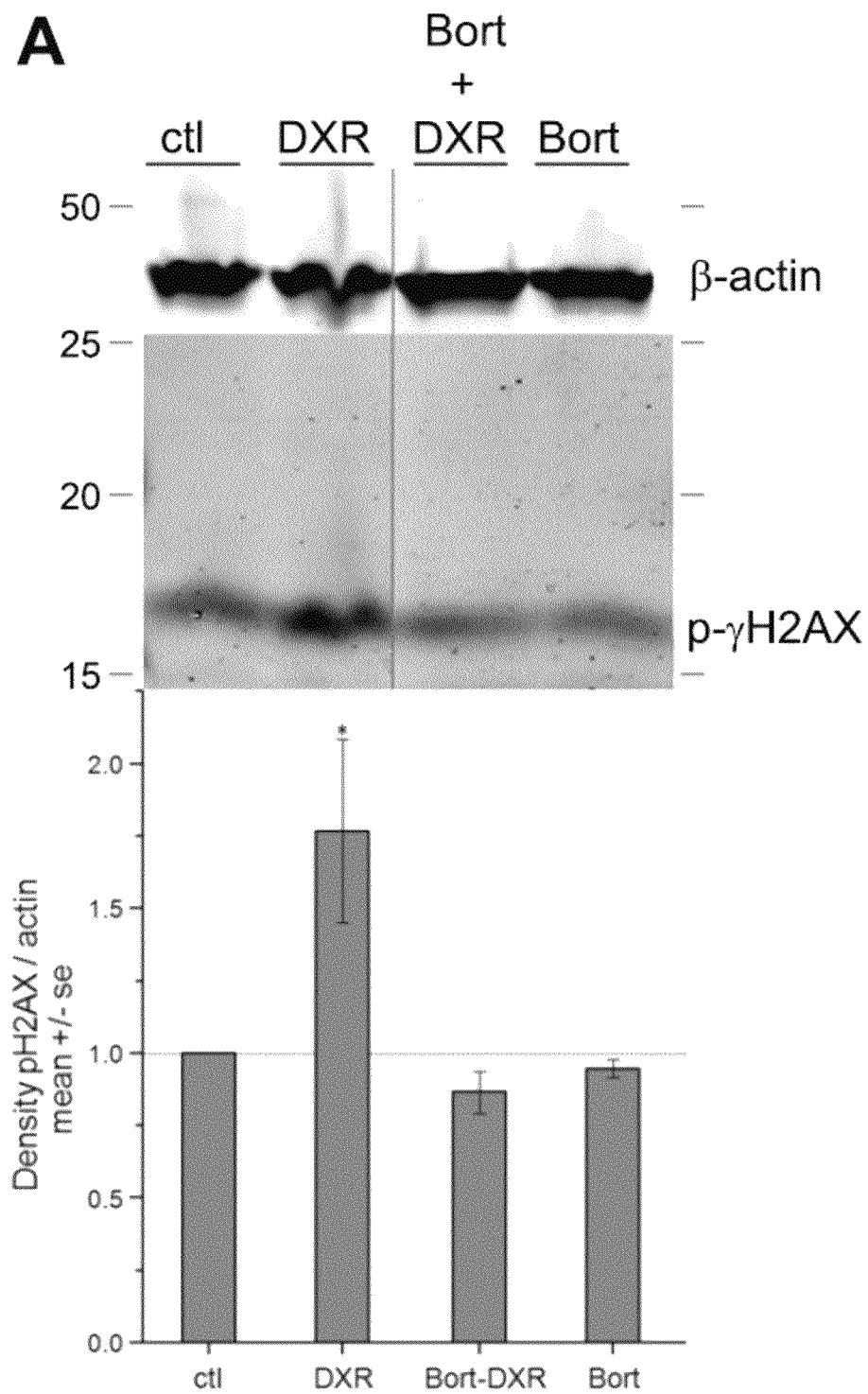
FIG. 9. Western blots with corresponding quantification reveal DXR-induced changes in γH2AX and pAKT phosphorylation, PTEN expression, and pro-Caspase-3. A. Blot probed with anti-phospho γH2AX antibodies reveal an increase in the corresponding 17 kDa band in ovarian lysates harvested 6 hrs post-DXR injection exclusively in DXR-treated mice. *$p<0.05$, one-way ANOVA, Tukey means comparison. B. Blot probed with anti-PTEN antibodies revealed a decrease in the density of the corresponding 60 kDa band in ovarian lysates harvested 6 hrs post-DXR injection exclusively in DXR-treated mice. C. Blot probed with anti-phospho-AKT1 antibodies revealed a decrease in the intensity of the corresponding 60 kDa band in ovarian lysates harvested 24 hrs post-DXR injection exclusively in DXR-treated mice. D. Blot probed with anti-Caspase 3 reveal a decrease in the intensity of the band corresponding to pro-Caspase 3, 24 hrs post-DXR injection exclusively in DXR-treated mice. All blots show β-actin as the loading control. N=3 blots/quantification.
Figure 9B:
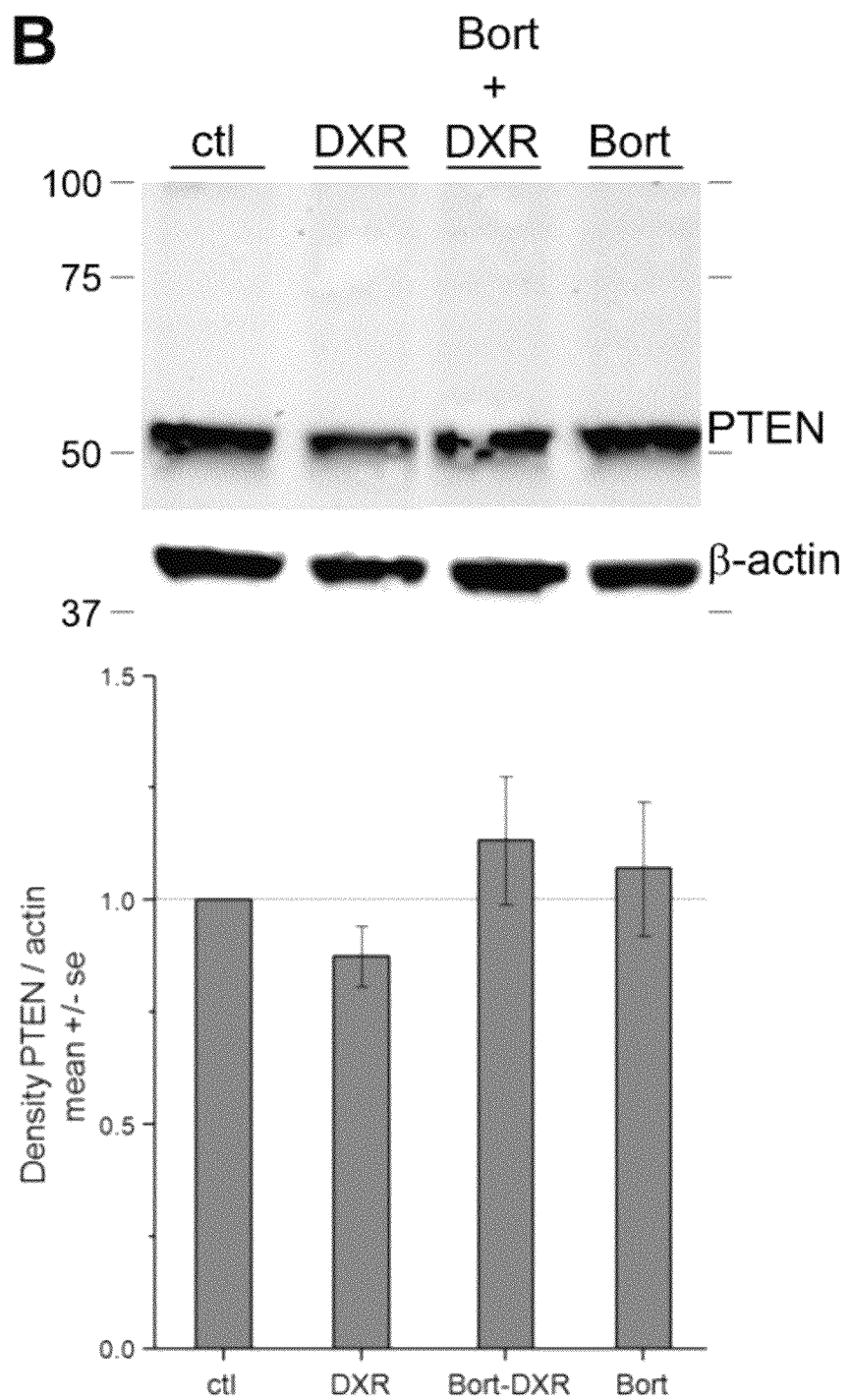
Figure 9C:
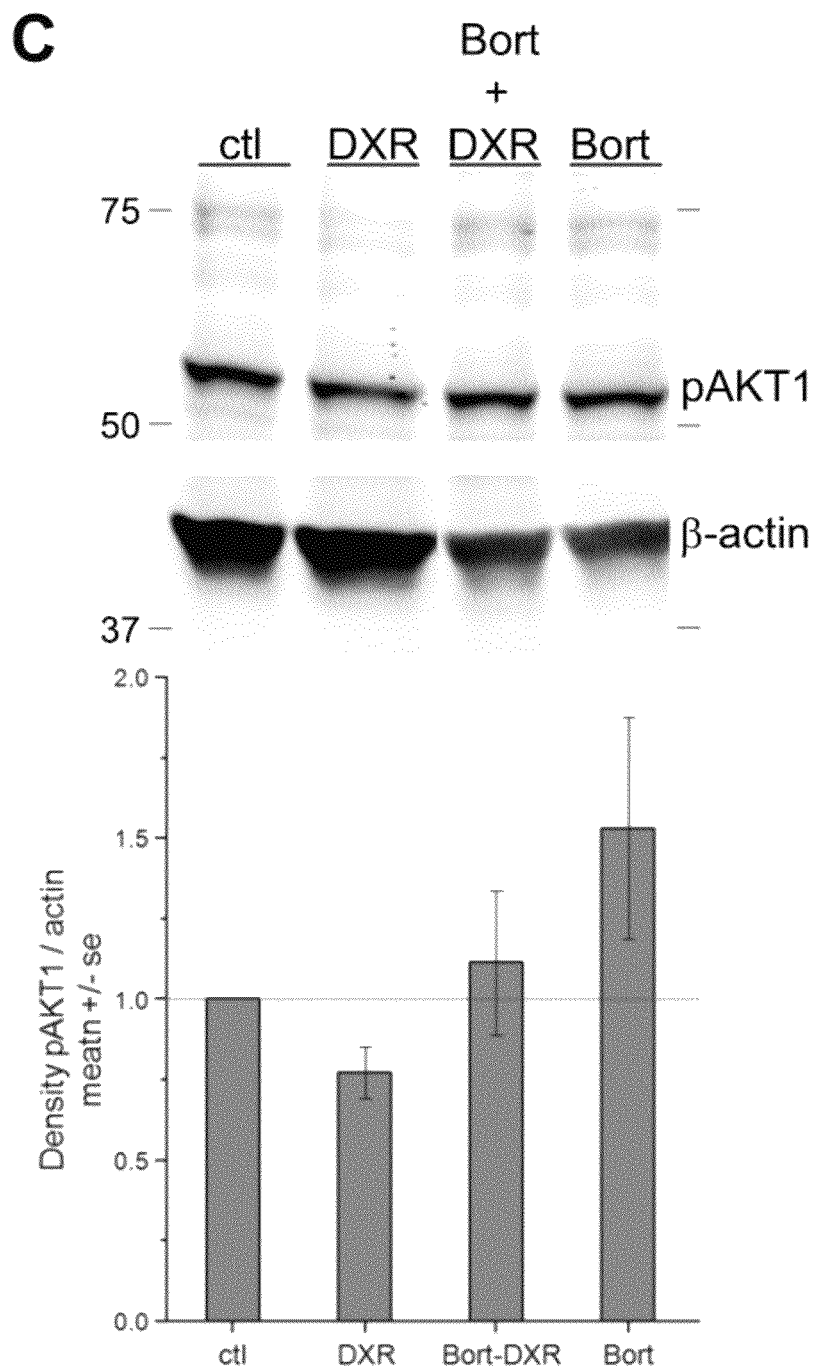
Figure 9D:
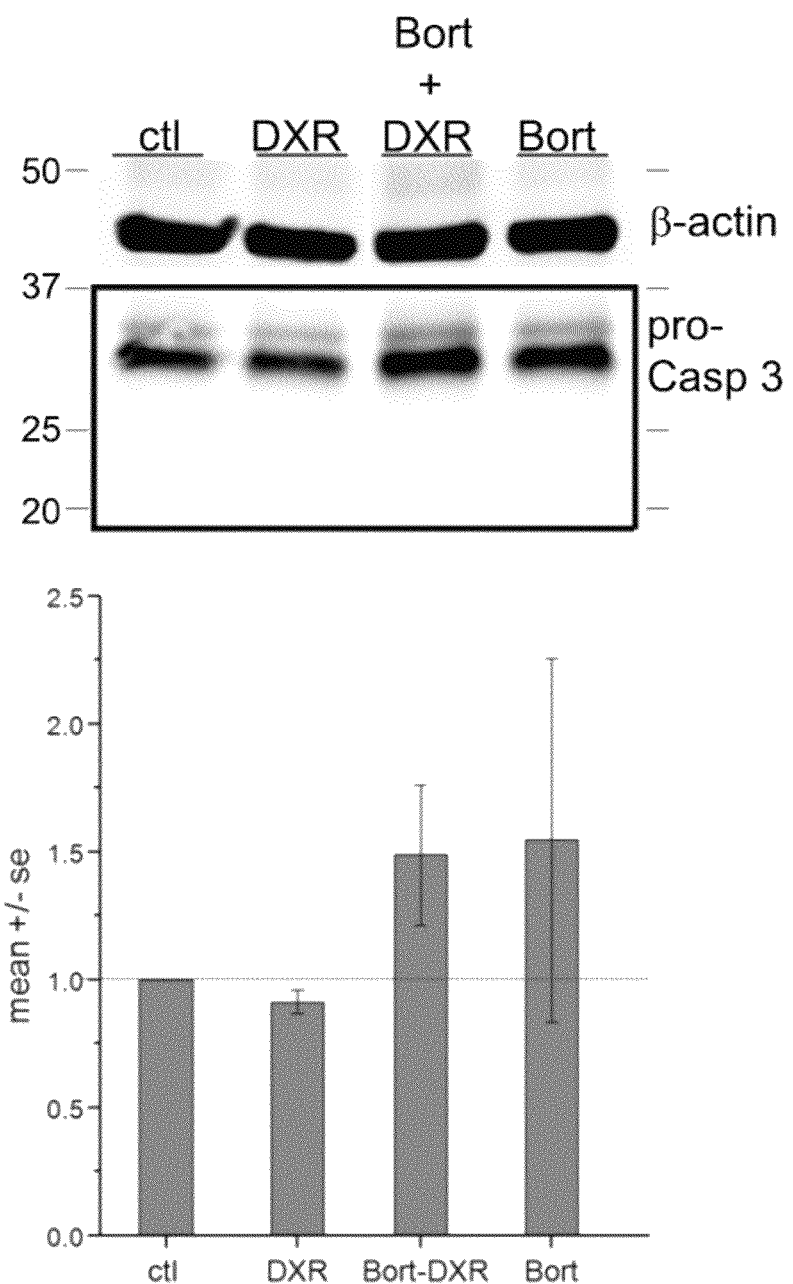

To determine whether Bort prevents the cellular response to DXR insult, Western blots (WBs) of ovarian lysates were probed for cell response markers at 6 and 24 hrs post-injection. Confirming the lack of DNA damage, Bort pretreatment attenuated DXR-induced γH2A.X phosphorylation (activation), the earliest cellular response to dsDNA breaks. DXR increased γH2A.X phosphorylation, demonstrated by an increase in intensity of the corresponding 17 kDa band on WBs of ovarian lysates harvested 6 hrs post-injection probed with anti-phospho-γH2A.X antibodies (FIG. 9a). The phospho-γH2A.X response was lacking in Bort-DXR and Bort-treated mice, demonstrating Bort prevented the earliest cellular response to DNA damage in the presence of DXR. Bort pretreatment appeared to similarly attenuate changes in PTEN and phoshpo-AKT expression induced by DXR. At 6 hrs post-injection, DXR treatment appeared to decrease PTEN protein expression levels, but with Bort pretreatment, PTEN protein reduction was eliminated (WBs, FIG. 9b). By 24 hrs post-injection, DXR also appeared to decrease phosphorylated (activated) AKT1 (pAKT1) levels in ovarian lysates (FIG. 9c), a loss which was similarly prevented by Bort pretreatment (FIG. 9c), consistent with cellular protection. Previous studies have shown DXR treatment results in activation of (cleavage) Caspase 3 in mouse ovaries [12]. Consistent with those data, we found a small decrease in the density of bands corresponding to full-length Caspase 3 following DXR treatment that was prevented by Bort (FIG. 9d). Though a cleaved Caspase 3 band was detected in D×R samples of some trials, it was not consistently dense enough for reliable quantification. Bort treatment alone did not significantly alter any of the proteins analyzed, suggesting that the drug is well-tolerated in ovarian tissue. Taken together, these data indicate Bort prevents DXR-induced changes in cellular survival pathways, consistent with ovarian protection.

To ascertain whether Bort pretreatment prevents DXR-induced follicular apoptosis, ovaries were harvested from mice treated with control vehicle, Bort, DXR, or Bort+DXR, 12 hrs after chemo administration. Under stringent scoring criteria labeling an entire follicle as apoptotic if it contained ≥4 TUNEL-positive granulosa cells [23], as Bort pretreatment resulted in a small decrease in the antral follicle apoptotic index compared to DXR alone, and significantly reduced the DXR-induced doubling of apoptotic-positive secondary follicles to levels not different from control (FIG. 10). Bort also decreased apoptosis in primary follicles indicating Bort attenuated DXR-induced follicular demise in vivo, preserving the growing preantral follicles key for subsequent fertility.

Figure 11A:
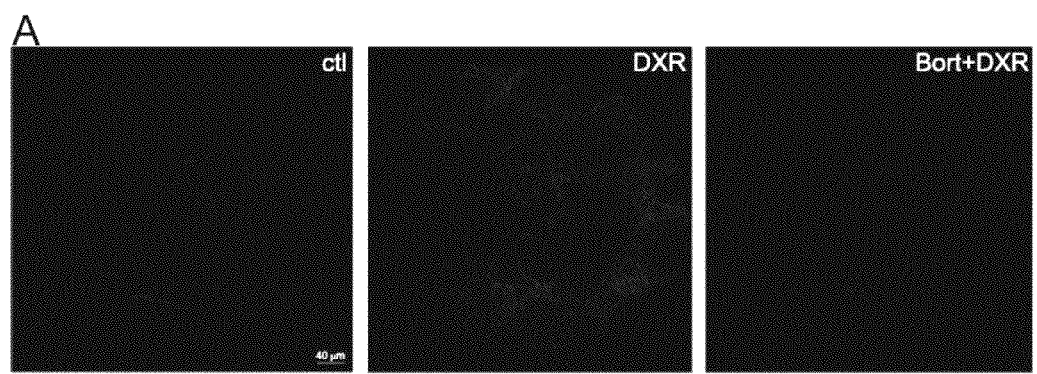
FIG. 11. Bort pretreatment prevented DXR accumulation in the mouse ovary. A. Micrographs of mouse ovarian sections obtained by spectral confocal imaging (ex. 488 nm, em. given in panel B). Images are overlays of all collected emission wavelengths. Bar=40 μm. For print, images were adjusted equally to a threshold of 140 in Photoshop with no other image enhancements. B. Graph plots mean fluorescence intensity+/−SEM quantified from raw DXR fluorescence in ovarian sections representing the top, middle, and bottom third of the ovary. Emission profiles at 550-560 nm (cold finger) were not collected by the microscope to prevent direct detection of the excitation laser at that wavelength. Confocal parameters were identical from one sample to the next. DXR points are statistically significant from ctl and Bort-DXR with $p<0.05$, one-way ANOVA, Bonferroni means comparison.
Figure 11B:
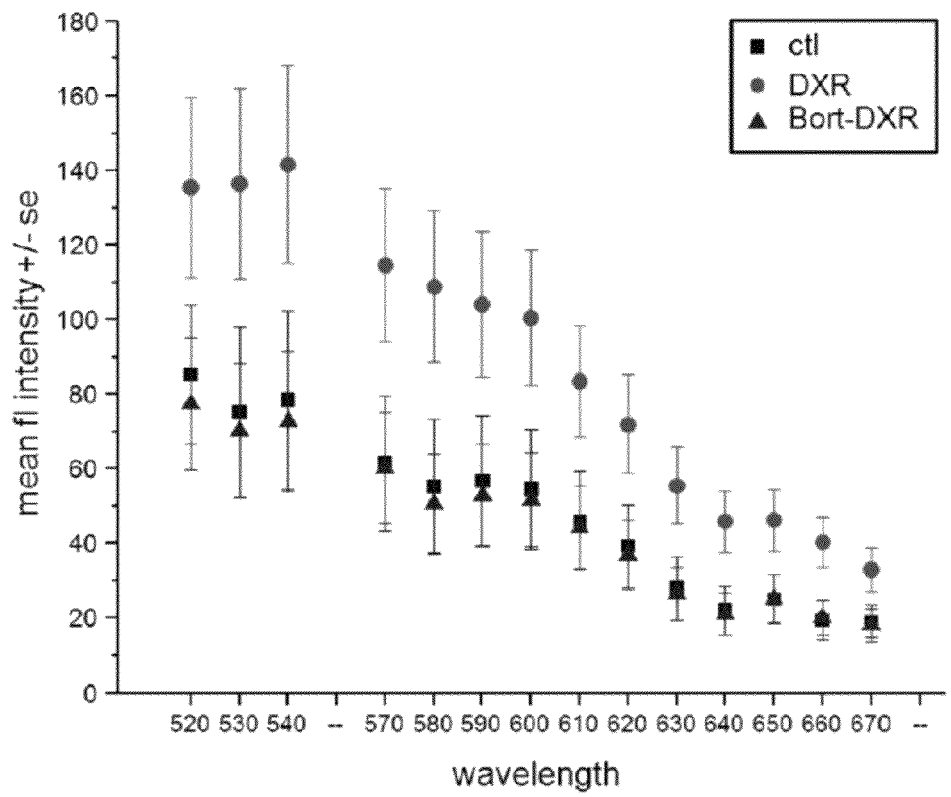

Previous studies by Kiyomona et al [17] demonstrate that DXR directly binds the proteasome; both binding and DXR nuclear transport and accumulation in vitro are blocked by proteasome inhibitors. To test the hypothesis that the mechanism by which Bort prevents DXR-induced DNA damage is reducing DXR accumulation in ovarian tissue, we quantified DXR in the ovary utilizing the drug's autofluorescence [13]. Spectral images of ovarian sections (FIG. 11a, spectral emission composites) demonstrated Bort pretreatment dropped DXR fluorescence to baseline levels (FIG. 11b, quantification). These data are consistent with a model in which Bort competition for proteasome binding prevents DXR entry to and accumulation within the cell nucleus. Further microscopy studies at higher magnification would facilitate analysis at the single cell level to distinguish nuclear from cytosolic DXR accumulation, but these data demonstrate a Bort-mediated lack of DXR fluorescence across the heterogeneous ovary, including all follicle types and stromal tissue.

This study demonstrates the clinically-approved anti-cancer proteasome inhibitor, Bort, is a promising candidate as an in vivo prophylactic to prevent anthracycline toxicity to the normal ovary. Future studies will test the efficacy of Bort in protecting the ovary from other chemo agents. The adolescent mice utilized in this study model a patient population for whom oncofertility treatments are limited. Pharma shields like Bort that prevent all markers of chemo-induced damage when given immediately prior to each chemo dose, should be effective regardless of patient age and cancer type, and thus have the potential to fill a gap in current oncofertility practices and compliment cryopreservation-based fertility technologies.

Adding to other fertoprotective agents under development including FTY720 and imatinib [24, 25], proteasome inhibitors represent ideal ovoprotective agents as the drugs were originally developed as anti-cancer agents and enhance, rather than interfere with, anti-tumor efficacy of traditional chemo agents [19]. Below the lowest human equivalent dose used in chemo regimens (heq 1.3 mg/m2), the Bort dose tested here (0.43 mg/m2) should be well-tolerated in patients. The ability to kill cancer cells while protecting normal tissue cells seems contradictory, but is based on the same therapeutic window concept that allows chemo to kill cancer without destroying the patient from which the original cancer arose. New generation proteasome inhibitors that increase anti-cancer potency and decrease the systemic side effects may provide further improvement over Bort as ovoprotective agents.

Bort blocked DXR-induced dsDNA breaks in all ovarian cell types, including oocytes, over the entire 24-hr acute injury period, but there was a small rise in comet moment in stromal cells from Bort-DXR mice at 2 hrs, followed by a drop back to baseline. Whether this represents transient DNA damage that is repaired, or a population of stromal cells that sustain damage, undergo necrosis, and hence are not detected at later time points can be assessed in future studies. Stromal cells isolated from DXR-treated mouse at 24 hrs in one of the three replicates showed an apparent decrease in comet moment, resulting in a drop of the mean. This was not observed in the large number of mice used in our initial characterization of acute DXR insult to the mouse ovary [13]. As previous work has demonstrated significant necrotic deterioration of stromal tissue by 12-24 hours post-DXR, it is most likely the apparent decrease in damage is loss of affected cells.

PTEN and AKT1 protein expression levels change in coordination following DXR treatment in a variety of cancer cells. In particular, AKT1 phosphorylation is linked to cell survival, and pAKT1 levels decrease in DXR-sensitive tumors following chemo treatment. In the present study, DXR treatment appeared to decrease levels of phosphorylated AKT1, consistent with decreased cell survival and the observed increase in TUNEL-positive cells. Bort pretreatment restored AKT1 phosphorylation to control levels, consistent with enhanced cell survival compared to DXR treatment alone, confirming effective ovarian protection. Quantifying DXR fluorescence revealed a lack of chemo accumulation in ovaries from mice pretreated with Bort.

Long-term fertility and fecundity assessment in mouse and nonhuman primate models can define Bort's development as an ovoprotective agent by determining whether acute protection translates to long-term preservation of ovarian and endocrine health. The efficacy of pairing Bort pretreatment with each DXR dose can also be determined in a traditional chemo schedule. The preservation of preantral follicles in the presence of Bort suggests that the prophylactic treatment can enable durable fertility and hormone function following DXR treatment.

To determine whether Bortezomib pretreatment increases female fertility, adolescent female (4 week old) CD-1 mice were injected with 10 mg/kg Doxorubicin with or without 1 hour pretreatment with 0.143 mg/kg Bortezomib. Both drugs were administered via i.p. injection. Female mice were then mated with proven fertile males starting at 8 weeks of age. Females were mated continuously with males, separated only for pup delivery, then re-mated immediately with rotated males. Pregnancy and litters were followed until females reached 8 months of age or became infertile.

Figure 12:
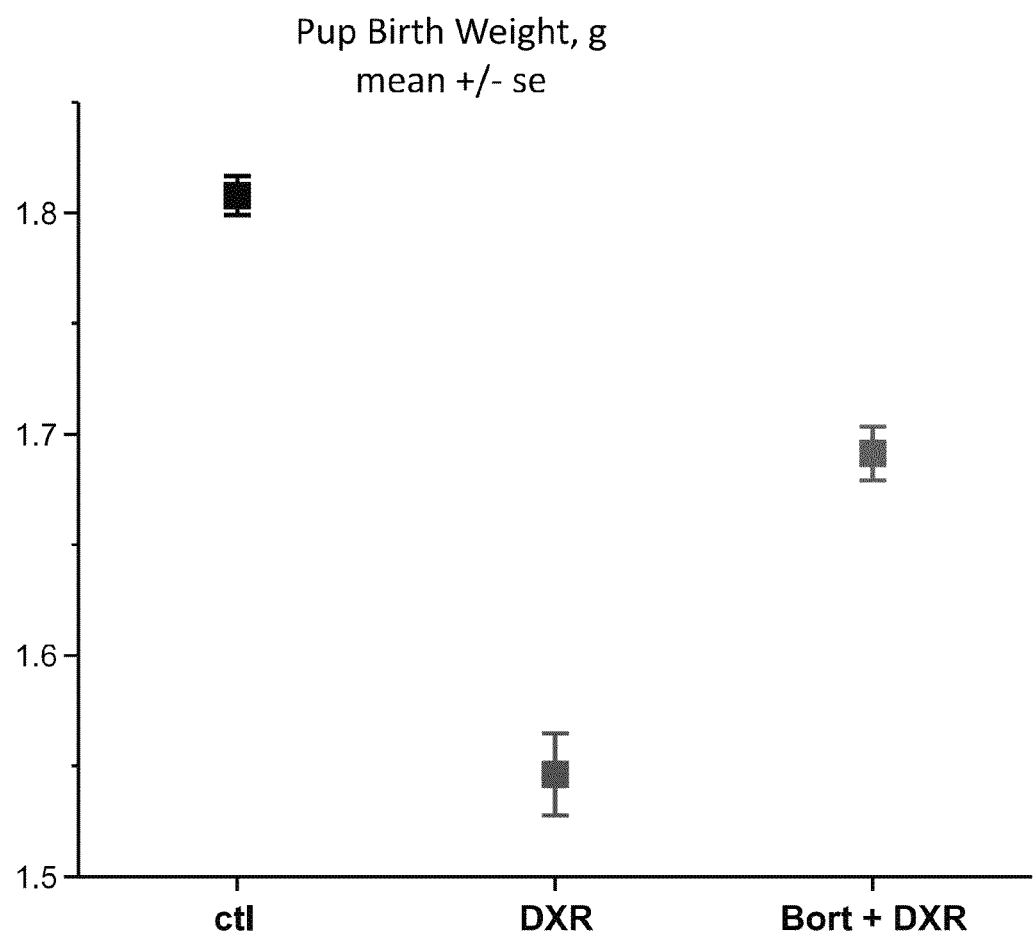
FIG. 12. DXR treatment decreased pup birth weight by 17% compared to controls. Bortezomib pretreatment restored pup weights to within 6% of control, statistically significantly greater than DXR-only birth weight.

DXR treatment decreased pup birth weight by 17% compared to controls (Stats, FIG. 12). Bortezomib pretreatment restored pup weights to within 6% of control, statistically significantly greater than DXR-only birth weight. These data indicate that Bortezomib pretreatment improves the general health of pups from female mice treated with DXR.

Figure 13:
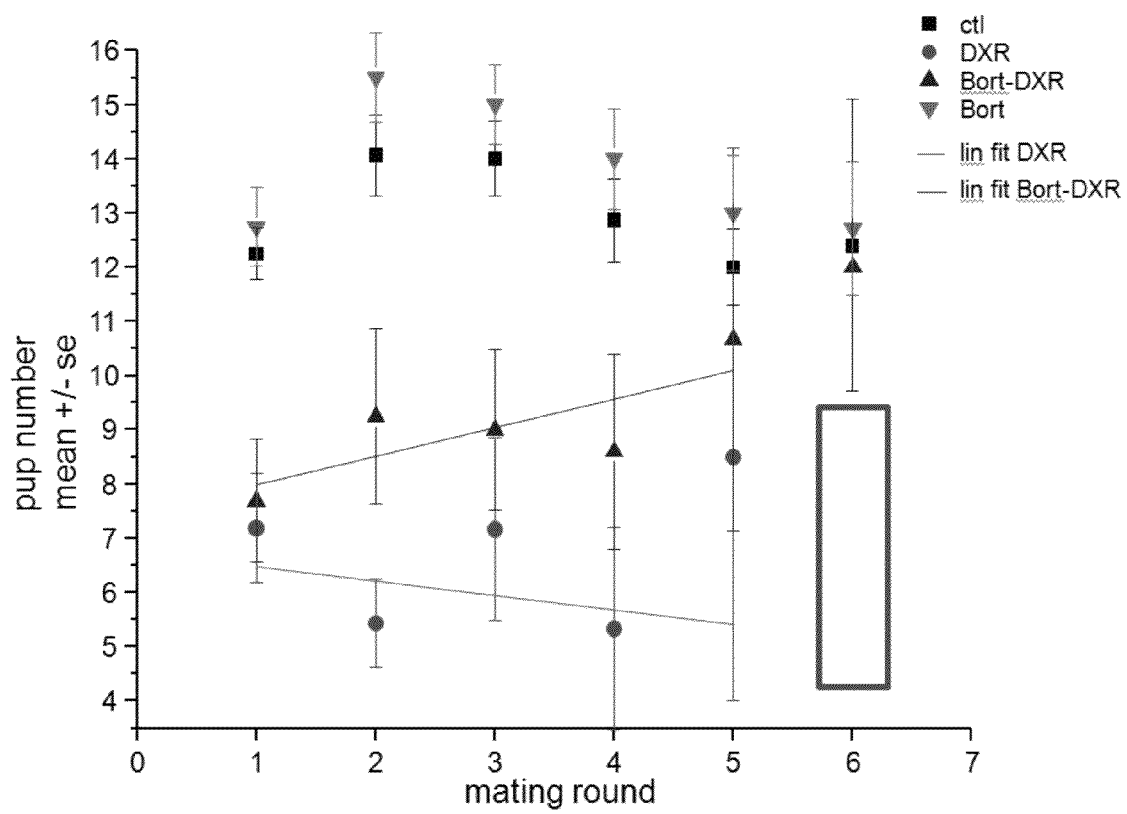
FIG. 13. DXR treatment dropped litter size to 50% of control. While the Bort-DXR treated mice also exhibited an initial decrease in litter size (8 pups in round 1), the litter size continuously increased over time with each mating round, to approach control levels by the end of the trial (12 pups, round 6).

Following litter size over mating round revealed that DXR dropped litter size to 50% of control (DXR: 5-8 pups/litter; ctl: 12-14 pups/litter FIG. 13). While the Bort-DXR treated mice also exhibited an initial decrease in litter size (8 pups in round 1), the litter size continuously increased over time with each mating round, to approach control levels by the end of the trial (12 pups, round 6, FIG. 13). These data are consistent with an initial loss of late antral follicles, followed by a replacement of mature follicles from Bort-protected pre-antral follicle pools (primordial, primary, and secondary follicles). Taken with the acute protection provided by Bortezomib, the in vivo breeding trials demonstrate the proteasome inhibitor sufficiently shields the ovary from DXR insult in such a way as to improve pup birth weight and litter size following DXR insult.

This study demonstrates Bort is a promising drug to serve as a prophylactic ovoprotective agent prior to DXR treatment and provides a model to develop additional drug-based approaches to preserve female reproductive health by preventing acute chemo insult. Drug-based chemoprotection has the potential to overcome current obstacles in oncofertility by preserving ovarian endocrine function regardless of reproductive maturity and cancer type. Cost-effective and easily administered in a non-invasive manner, such ovoprotective agents may thus prevent long-term health complications currently associated with chemo-induced premature menopause.

REFERENCES

1. Bagchi A, Woods E J, Critser J K. Cryopreservation and vitrification: recent advances in fertility preservation technologies. Expert review of medical devices 2008; 5:359-370.
2. Bromer J G, Patrizio P. Fertility Preservation: The Rationale for Cryopreservation of the Whole Ovary. Seminars In Reproductive Medicine 2009; 27:465-471.
3. Cao Y X, Chian R C. Fertility Preservation with Immature and in Vitro Matured Oocytes. Seminars In Reproductive Medicine 2009; 27:456-464.
4. Donnez J. Advances in fertility preservation for children and adolescents with cancer. European Journal of Cancer 2009; 45 Suppl 1:418.
5. Ata B, Chian R C, Tan S L. Cryopreservation of oocytes and embryos for fertility preservation for female cancer patients. Best practice & research. Clinical obstetrics & gynaecology 2010; 24:101-112.
6. Oktay K, Oktem O, Reh A, Vandat L. Measuring the impact of chemotherapy on fertility in women with breast cancer. Journal of clinical oncology: official journal of the American Society of Clinical Oncology 2006; 24:4044-4046.
7. Oktay K, Oktem O. Fertility preservation medicine: a new field in the care of young cancer survivors. Pediatric blood & cancer 2009; 53:267-273.
8. Hewitt M, Breen N, Devesa S. Cancer prevalence and survivorship issues: Analyses of the 1992 National Health Interview Survey. Journal of the National Cancer Institute 1999; 91:1480-1486.
9. Chow W H, Dong L M, Devesa S S. Epidemiology and risk factors for kidney cancer. Nature reviews. Urology 2010; 7:245-257.
10. Smith M A, Freidlin B, Ries L A, Simon R. Trends in reported incidence of primary malignant brain tumors in children in the United States. Journal of the National Cancer Institute 1998; 90:1269-1277.
11. Society AC. Cancer Facts and Figures 2011. http://www.cancer.gov/cancertopics/factsheet/Sites-Types/childhood 2011.
12. Alharbi M M, Algharably N M, Alshabanah O A, Albekairi A M, Osman A M M, Tawfik H N. Prevention Of Doxorubicin-Induced Myocardial And Hematological Toxicities In Rats By The Iron Chelator Desferrioxamine. Cancer Chemotherapy And Pharmacology 1992; 31:200-204.
13. Gewirtz D A. A critical evaluation of the mechanisms of action proposed for the antitumor effects of the anthracycline antibiotics Adriamycin and daunorubicin. Biochemical Pharmacology 1999; 57:727-741.
14. Hershko C, Link G, Tzahor M, Kaltwasser J P, Athias P, Grynberg A, Pinson A. Anthracycline Toxicity Is Potentiated By Iron And Inhibited By Deferoxamine—Studies In Rat-Heart Cells In Culture. Journal Of Laboratory And Clinical Medicine 1993; 122:245-251.
15. Hasinoff B. Dexrazoxane (ICRF-187) protects cardiac myocytes against hypoxia-reoxygenation damage. Cardiovascular Toxicology 2002; 2:111-118.
16. Hasinoff B B, Schroeder P E, Patel D. The metabolites of the cardioprotective drug dexrazoxane do not protect myocytes from doxorubicin-induced cytotoxicity. Molecular Pharmacology 2003; 64:670-678.
17. Swift L M, Sarvazyan N. Localization of dichlorofluorescin in cardiac myocytes: implications for assessment of oxidative stress. American Journal of Physiology-Heart and Circulatory Physiology 2000; 278:H982-H990.
18. Voest E E, Vanacker S, Vandervijgh W J F, Vanasbeck B S, Bast A. Comparison Of Different Iron Chelators As Protective Agents Against Acute Doxorubicin-Induced Cardiotoxicity. Journal Of Molecular And Cellular Cardiology 1994; 26:1179-1185.
19. Roti Roti E C, Salih S M. Dexrazoxane ameliorates doxorubicin-induced injury in mouse ovarian cells. Biology of Reproduction 2012; 86:1-11.
20. Bar-Joseph H, Ben-Aharon I, Rizel S, Stemmer S M, Tzabari M, Shalgi R. Doxorubicin-induced apoptosis in germinal vesicle (G V) oocytes. Reproductive Toxicology 2010; 30:566-572.
21. Ben-Aharon I, Bar-Joseph H, Tzarfaty G, Kuchinsky L, Rizel S, Stemmer S M, Shalgi R. Doxorubicin-induced ovarian toxicity. Reproductive Biology And Endocrinology 2010; 8.
22. Kujjo L L, Chang E A, Pereira R J G, Dhar S, Marrero-Rosado B, Sengupta S, Wang H B, Cibelli J B, Perez G I. Chemotherapy-Induced Late Transgenerational Effects in Mice. Plos One 2011; 6.

23. Kerr J B, Brogan L, Myers M, Hutt K J, Mladenovska T, Ricardo S, Hamza K, Scott C L, Strasser A, Findlay J K. The primordial follicle reserve is not renewed after chemical or gamma-irradiation mediated depletion. Reproduction 2012; 143:469-476.

24. Praet M, Pollakis G, Goormaghtigh E, Ruysschaert J M. Damages of the mitochondrial membrane in Adriamycin treated mice. Cancer Letters 1984; 25:89-96.

25. Ben-Aharon I, Bar-Joseph H, Tzarfaty G, Kuchinsky L, Rizel S, Stemmer S M, Shalgi R. Doxorubicin-induced ovarian toxicity. Reproductive biology and endocrinology: RB&E 2010; 8:20.

26. Mukhopadhyay P, Rajesh M, Batkai S, Kashiwaya Y, Hasko G, Liaudet L, Szabo C, Pacher P. Role of superoxide, nitric oxide, and peroxynitrite in doxorubicin-induced cell death in vivo and in vitro. American journal of physiology. Heart and circulatory physiology 2009; 296:H1466-1483.

27. Panaretakis T, Pokrovskaja K, Shoshan M C, Grander D. Activation of Bak, Bax, and B H3-only proteins in the apoptotic response to doxorubicin. Journal of Biological Chemistry 2002; 277:44317-44326.

28. Perez G I, Knudson C M, Leykin L, Korsmeyer S J, Tilly J L. Apoptosis-associated signaling pathways are required for chemotherapy-mediated female germ cell destruction. Nature Medicine 1997; 3:1228-1232.

29. Sergeev I N, Norman A W. Calcium as a mediator of apoptosis in bovine oocytes and preimplantation embryos. Endocrine 2003; 22:169-175.

30. Perez G I, Tao X J, Tilly J L. Fragmentation and death (a.k.a. apoptosis) of ovulated oocytes. Molecular Human Reproduction 1999; 5:414-420.

31. Bonilla E, del Mazo J. Deregulation of gene expression in fetal oocytes exposed to doxorubicin. Biochemical Pharmacology 2003; 65:1701-1707.

32. Roti Roti E C, Leisman S K, Abbott D H, Salih S M. Acute Doxorubicin Insult in the Mouse Ovary Is Cell- and Follicle-Type Dependent. Plos One 2012; 7.

33. Kiyomiya K, Matsuo S, Kurebe M. Proteasome is a carrier to translocate doxorubicin from cytoplasm into nucleus. Life Sciences 1998; 62:1853-1860.

34. Kiyomiya K I, Satoh J, Horie H, Kurebe M, Nakagawa H, Matsuo S. Correlation between nuclear action of anthracycline anticancer agents and their binding affinity to the proteasome. International Journal Of Oncology 2002; 21:1081-1085.

35. Baumeister W, Walz J, Zuhl F, Seemuller E. The proteasome: paradigm of a self-compartmentalizing protease. Cell 1998; 92:367-380.

36. Nederlof P M, Wang H R, Baumeister W. Nuclear localization signals of human and Thermoplasma proteasomal alpha subunits are functional in vitro. Proceedings of the National Academy of Sciences of the United States of America 1995; 92:12060-12064.

37. Kiyomiya K, Matsuo S, Kurebe M. In situ photoaffinity labeling of proteasome with photoactive adriamycin analogue. Biochemical And Biophysical Research Communications 2000; 273:928-932.

38. Kiyomiya K, Matsuo S, Kurebe M. Mechanism of specific nuclear transport of adriamycin: The mode of nuclear translocation of adriamycin-proteasome complex. Cancer Research 2001; 61:2467-2471.

39. Lyu Y L, Kerrigan J E, Lin C P, Azarova A M, Tsai Y C, Ban Y, Liu L F. Topoisomerase II beta-Mediated DNA double-strand breaks: Implications in doxorubicin cardiotoxicity and prevention by dexrazoxane. Cancer Research 2007; 67:8839-8846.

40. Huang H B, Liu N N, Yang C S, Liao S Y, Guo H P, Zhao K, Li X F, Liu S T, Guan L X, Liu C J, Xu L, Zhang C G, et al. HDAC Inhibitor L-Carnitine and Proteasome Inhibitor Bortezomib Synergistically Exert Anti-Tumor Activity In Vitro and In Vivo. Plos One 2012; 7.

41. Ludwig H, Viterbo L, Greil R, Masszi T, Spicka I, Shpilberg O, Hajek R, Dmoszynska A, Paiva B, Vidriales M B, Esteves G, Stoppa A M, et al. Randomized Phase II Study of Bortezomib, Thalidomide, and Dexamethasone With or Without Cyclophosphamide As Induction Therapy in Previously Untreated Multiple Myeloma. Journal of Clinical Oncology 2013; 31:247-255.

42. White D, Kassim A, Bhaskar B, Yi J, Wamstad K, Paton V E. Results from AMBER, a randomized phase 2 study of bevacizumab and bortezomib versus bortezomib in relapsed or refractory multiple myeloma. Cancer 2013; 119:339-347.

43. Zuo J, Bi C F, Fan Y H, Buac D, Nardon C, Daniel K G, Dou Q P. Cellular and computational studies of proteasome inhibition and apoptosis induction in human cancer cells by amino acid Schiff base-copper complexes. Journal of Inorganic Biochemistry 2013; 118:83-93.

44. Huang C M, Hu X X, Wang L B, Lu S Q, Cheng H, Song X M, Wang J M, Yang J M. Bortezomib suppresses the growth of leukemia cells with Notch1 overexpression in vivo and in vitro. Cancer Chemotherapy and Pharmacology 2012; 70:801-809.

45. Wunderlich A, Roth S, Ramaswamy A, Greene B H, Brendel C, Hinterseher U, Bartsch D K, Hoffmann S. Combined inhibition of cellular pathways as a future therapeutic option in fatal anaplastic thyroid cancer. Endocrine 2012; 42:637-646.

46. Abaza M S I, Bahman A M, Al-Attiyah R J, Kollamparambil A M. Synergistic induction of apoptosis and chemosensitization of human colorectal cancer cells by histone deacetylase inhibitor, scriptaid, and proteasome inhibitors: potential mechanisms of action. Tumor Biology 2012; 33:1951-1972.

47. Jung H J, Chen Z, McCarty N. Synergistic anticancer effects of arsenic trioxide with bortezomib in mantle cell lymphoma. American Journal of Hematology 2012; 87:1057-1064.

48. Lawasut P, Chauhan D, Laubach J, Hayes C, Fabre C, Maglio M, Mitsiades C, Hideshima T, Anderson K, Richardson P. New Proteasome Inhibitors in Myeloma. Current Hematologic Malignancy Reports 2012; 7:258-266.

49. Millward M, Price T, Townsend A, Sweeney C, Spencer A, Sukumaran S, Longenecker A, Lee L, Lay A, Sharma G, Gemmill R M, Drabkin H A, et al. Phase 1 clinical trial of the novel proteasome inhibitor marizomib with the histone deacetylase inhibitor vorinostat in patients with melanoma, pancreatic and lung cancer based on in vitro assessments of the combination. Investigational New Drugs 2012; 30:2303-2317.

50. Nie D N, Huang K Z, Yin S M, Li Y Q, Xie S F, Ma L P, Wang X J, Wu Y D, Xiao J. Synergistic/additive interaction of valproic acid with bortezomib on proliferation and apoptosis of acute myeloid leukemia cells. Leukemia & Lymphoma 2012; 53:2487-2495.

51. Sato A, Asano T, Ito K. Vorinostat and Bortezomib Synergistically Cause Ubiquitinated Protein Accumulation in Prostate Cancer Cells. Journal of Urology 2012; 188:2410-2418.

52. Altmann A, Markert A, Askoxylakis V, Schoning T, Jesenofsky R, Eisenhut M, Haberkorn U. Antitumor Effects of Proteasome Inhibition in Anaplastic Thyroid Carcinoma. Journal of Nuclear Medicine 2012; 53:1764-1771.

53. Amodio N, Di Martino M T, Foresta U, Leone E, Lionetti M, Leotta M, Gulla A M, Pitari M R, Conforti F, Rossi M, Agosti V, Fulciniti M, et al. miR-29b sensitizes multiple myeloma cells to bortezomib-induced apoptosis through the activation of a feedback loop with the transcription factor Sp 1. Cell Death & Disease 2012; 3.
54. Hui B, Shi Y H, Ding Z B, Zhou J, Gu C Y, Peng Y F, Yang H, Liu W R, Shi G M, Fan J. Proteasome Inhibitor Interacts Synergistically With Autophagy Inhibitor to Suppress Proliferation and Induce Apoptosis in Hepatocellular Carcinoma. Cancer 2012; 118:5560-5571.
55. Maynadier M, Shi J X, Vaillant O, Gary-Bobo M, Basile I, Gleizes M, Cathiard A M, Wah J L T, Sheikh M S, Garcia M. Roles of Estrogen Receptor and p21(Waf1) in Bortezomib-Induced Growth Inhibition in Human Breast Cancer Cells. Molecular Cancer Research 2012; 10:1473-1481.
56. Jones D R, Moskaluk C A, Gillenwater H H, Petroni G R, Burks S G, Philips J, Rehm P K, Olazagasti J, Kozower B D, Bao Y D. Phase I Trial of Induction Histone Deacetylase and Proteasome Inhibition Followed by Surgery in Non-Small-Cell Lung Cancer. Journal of Thoracic Oncology 2012; 7:1683-1690.
57. Mizuno H, Nakayama T, Miyata Y, Saito S, Nishiwaki S, Nakao N, Takeshita K, Naoe T. Mast cells promote the growth of Hodgkin's lymphoma cell tumor by modifying the tumor microenvironment that can be perturbed by bortezomib. Leukemia 2012; 26:2269-2276.
58. Yerlikaya A, Okur E, Ulukaya E. The p53-independent induction of apoptosis in breast cancer cells in response to proteasome inhibitor bortezomib. Tumor Biology 2012; 33:1385-1392.
59. Fennell D A, McDowell C, Busacca S, Webb G, Moulton B, Cakana A, O'Byrne K J, Meerbeeck J V, Donnellan P, McCaffrey J, Baas P. Phase II Clinical Trial of First or Second-Line Treatment with Bortezomib in Patients with Malignant Pleural Mesothelioma. Journal of Thoracic Oncology 2012; 7:1466-1470.
60. Hu W, Zheng R R, Cui H X, Yue D, Wang Y, Jiang Y H. Effects of bortezomib in sensitizing human prostate cancer cell lines to N K-mediated cytotoxicity. Asian Journal of Andrology 2012; 14:695-702.
61. Wang M, Halasi M, Kabirov K, Banerjee A, Landolfi J, Lyubimov A V, Gartel A L. Combination treatment with bortezomib and thiostrepton is effective against tumor formation in mouse models of DEN/PB-induced liver carcinogenesis. Cell Cycle 2012; 11:3370-3372.
62. Wang Y D, Ai L S, Cui G H, Gowrea B, Li M, Hu Y. Once-versus twice-weekly Bortezomib induction therapy with dexamethasone in newly diagnosed multiple myeloma. Journal of Huazhong University of Science and Technology-Medical Sciences 2012; 32:495-500.
63. Gatti L, Benedetti V, De Cesare M, Coma E, Cincinelli R, Zaffaroni N, Zunino F, Perego P. Synergistic interaction between the novel histone deacetylase inhibitor ST2782 and the proteasome inhibitor bortezomib in platinum-sensitive and resistant ovarian carcinoma cells. Journal of Inorganic Biochemistry 2012; 113:94-101.
64. Sinha R, Kaufman J L, Khoury H J, King N, Shenoy P J, Lewis C, Bumpers K, Hutchison-Rzepka A, Tighiouart M, Heffner L T, Lechowicz M J, Lonial S, et al. A phase 1 dose escalation study of bortezomib combined with rituximab, cyclophosphamide, doxorubicin, modified vincristine, and prednisone for untreated follicular lymphoma and other low-grade B-cell lymphomas. Cancer 2012; 118:3538-3548.
65. Lenz H J. Clinical update: proteasome inhibitors in solid tumors. Cancer Treatment Reviews 2003; 29:41-48.
66. Richardson P. Clinical update: proteasome inhibitors in hematologic malignancies. Cancer Treatment Reviews 2003; 29:33-39.
67. Schenkein D. Proteasome inhibitors in the treatment of B-cell malignancies. Clinical Lymphoma 2002; 3:49-55.
68. Fally B N, Schlieman M G, Virudachalam S, Bold R J. Schedule-dependent molecular effects of the proteasome inhibitor bortezomib and gemcitabine in pancreatic cancer. Journal of Surgical Research 2003; 113:88-95.
69. Ling Y H, Liebes L, Zou Y Y, Perez-Soler R. Reactive oxygen species generation and mitochondrial dysfunction in the apoptotic response to bortezomib, a novel proteasome inhibitor, in human H460 non-small cell lung cancer cells. Journal of Biological Chemistry 2003; 278:33714-33723.
70. Pahler J C, Ruiz S, Niemer I, Calvert L R, Andreeff M, Keating M, Faderl S, McConkey D J. Effects of the proteasome inhibitor, bortezomib, on apoptosis in isolated lymphocytes obtained from patients with chronic lymphocytic leukemia. Clinical Cancer Research 2003; 9:4570-4577.
71. Richardson P G, Barlogie B, Berenson J, Singhal S, Jagannath S, Irwin D, Rajkumar S V, Srkalovic G, Alsina M, Alexanian R, Siegel D, Orlowski R Z, et al. A phase 2 study of bortezomib in relapsed, refractory myeloma. New England Journal of Medicine 2003; 348:2609-2617.
72. Williams S, Pettaway C, Song R, Papandreou C, Logothetis C, McConkey D J. Differential effects of the proteasome inhibitor bortezomib on apoptosis and angiogenesis prostate tumor xenografts. Molecular Cancer Therapeutics 2003; 2:835-843.
73. Adams J, Kauffman M. Development of the proteasome inhibitor Veleade™ (Bortezomib). Cancer Investigation 2004; 22:304-311.
74. Dai Y, Rahmani M, Grant S. Proteasome inhibitors potentiate leukemic cell apoptosis induced by the cyclin-dependent kinase inhibitor flavopiridol through a SAPK/JNK- and NF-kappa B-dependent process. Oncogene 2003; 22:7108-7122.
75. Kamat A M, Karashima T, Davis D W, Lashinger L, Bar-Eli M, Millikan R, Shen Y, Dinney C P N, McConkey D J. The proteasome inhibitor bortezomib synergizes with gemcitabine to block the growth of human 253JB-V bladder tumors in vivo. Molecular Cancer Therapeutics 2004; 3:279-290.
76. Nawrocki S T, Sweeney-Gotsch B, Takamori R, McConkey D J. The proteasome inhibitor bortezomib enhances the activity of docetaxel in orthotopic human pancreatic tumor xenografts. Molecular Cancer Therapeutics 2004; 3:59-70.
77. Park D J, Lenz H J. The role of proteasome inhibitors in solid tumors Annals of Medicine 2004; 36:296-303.
78. Richardson P G, Hideshima T, Mitsiades C, Anderson K. Proteasome inhibition in hematologic malignancies. Annals of Medicine 2004; 36:304-314.
79. Yu J, Tiwari S, Steiner P, Zhang L. Differential apoptotic response to the proteasome inhibitor bortezomib (VELCADE™, PS-341) in bax-deficient and p21-deficient colon cancer cells. Cancer Biology & Therapy 2003; 2:694-699.
80. Zwergel T, Tahmatzopoulos A, Wullich B, Zwergel U, Stockle M, Unteregger G. Proteasome inhibitors and their combination with antiandrogens: effects on apoptosis, cellular proliferation and viability of prostatic adenocarcinoma cell cultures. Prostate Cancer and Prostatic Diseases 2004; 7:138-143.
81. Adachi M, Zhang Y B, Zhao X D, Minami T, Kawamura R, Hinoda Y, Imai K. Synergistic effect of histone deacetylase inhibitors FK228 and m-carboxycinnamic acid bis-hydroxamide with proteasome inhibitors PSI and PS-341 against gastrointestinal adenocarcinoma cells. Clinical Cancer Research 2004; 10:3853-3862.
82. Cortes J, Thomas D, Koller C, Giles F, Estey E, Faderl S, Garcia-Manero G, McConkey D, Patel G, Guerciolini R, Wright J, Kantarjian H. Phase I study of bortezomib in refractory or relapsed acute leukemias. Clinical Cancer Research 2004; 10:3371-3376.
83. Denlinger C E, Keller M D, Mayo M W, Broad R M, Jones D R. Combined proteasome and histone deacetylase inhibition in non-small cell lung cancer. Journal of Thoracic and Cardiovascular Surgery 2004; 127:1078-1086.
84. Papandreou C N, Daliani D D, Nix D, Yang H, Madden T, Wang X M, Pien C S, Millikan R E, Tu S M, Pagliaro L, Kim J, Adams J, et al. Phase I trial of the proteasome inhibitor bortezomib in patients with advanced solid tumors with observations in androgen-independent prostate cancer. Journal of Clinical Oncology 2004; 22:2108-2121.
85. Pei X Y, Dai Y, Grant S. Synergistic induction of oxidative injury and apoptosis in human multiple myeloma cells by the proteasome inhibitor bortezomib and histone deacetylase inhibitors. Clinical Cancer Research 2004; 10:3839-3852.
86. Sun K, Welniak L A, Panoskaltsis-Mortari A, O'Shaughnessy M J, Liu H Y, Barao I, Riordan W, Sitcheran R, Wysocki C, Serody J S, Blazar B R, Sayers T J, et al. Inhibition of acute graft-versus-host disease with retention of graft-versus-tumor effects by the proteasome inhibitor bortezomib. Proceedings of the National Academy of Sciences of the United States of America 2004; 101:8120-8125.
87. Amiri K I, Horton L W, LaFleur B J, Sosman J A, Richmond A. Augmenting chemosensitivity of malignant melanoma tumors via proteasome inhibition: Implication for bortezomib (VELCADE, PS-341) as a therapeutic agent for malignant melanoma. Cancer Research 2004; 64:4912-4918.
88. An J, Sun Y, Fisher M, Rettig M B. Antitumor effects of bortezomib (PS-341) on primary effusion lymphomas. Leukemia 2004; 18:1699-1704.
89. Denlinger C E, Rundall B K, Keller M D, Jones D R. Proteasome inhibition sensitizes non-small-cell lung cancer to gemcitabine-induced apoptosis Annals of Thoracic Surgery 2004; 78:1207-1214.
90. Mortenson M M, Schlieman M G, Virudachalam S, Bold R J. Effects of the proteasome inhibitor bortezomib alone and in combination with chemotherapy in the A549 non-small-cell lung cancer cell line. Cancer Chemotherapy and Pharmacology 2004; 54:343-353.
91. Shah M H, Young D, Kindler H L, Webb I, Kleiber B, Wright J, Greyer M. Phase II study of the proteasome inhibitor bortezomib (PS-341) in patients with metastatic neuroendocrine tumors. Clinical Cancer Research 2004; 10:6111-6118.
92. Blaney S M, Bernstein M, Neville K, Ginsberg J, Kitchen B, Horton T, Berg S L, Krailo M, Adamson P C. Phase I study of the proteasome inhibitor bortezomib in pediatric patients with refractory solid tumors: A children's oncology group study (ADVL0015). Journal of Clinical Oncology 2004; 22:4804-4809.
93. Brooks A D, Ramirez T, Toh U, Onksen J, Elliott P J, Murphy W J, Sayers T J. The proteasome inhibitor bortezomib (Velcade) sensitizes some human tumor cells to Apo2L/TRAIL-mediated apoptosis. In: ElDeiry W S (ed.) Tumor Progression and Therapeutic Resistance, vol. 1059; 2005: 160-167.
94. Denlinger C E, Rundall B K, Jones D R. Proteasome inhibition sensitizes non-small cell lung cancer to histone deacetylase inhibitor-induced apoptosis through the generation of reactive oxygen species. Journal of Thoracic and Cardiovascular Surgery 2004; 128:740-748.
95. Fribley A, Zeng Q H, Wang C Y. Proteasome inhibitor PS-341 induces a apoptosis through induction of endoplasmic reticulum stress-reactive oxygen species in head and neck squamous cell carcinoma cells. Molecular and Cellular Biology 2004; 24:9695-9704.
96. Matta H, Chaudhary P M. The proteasome inhibitor bortezomib (PS-341) inhibits growth and induces apoptosis in primary effusion lymphoma cells. Cancer Biology & Therapy 2005; 4:77-82.
97. Papageorgiou A, Lashinger L, Millikan R, Grossman H B, Benedict W, Dinney CPN, McConkey D J. Role of tumor necrosis factor-related apoptosis-inducing ligand in interferon-induced apoptosis in human bladder cancer cells. Cancer Research 2004; 64:8973-8979.
98. Jagannath S, Barlogie B, Berenson J R, Singhal S, Alexanian R, Srkalovic G, Orlowski R Z, Richardson P G, Anderson J, Nix D, Esseltine D L, Anderson K C, et al. Bortezornib in recurrent and/or refractory multiple myeloma—Initial clinical experience in patients with impaired renal function. Cancer 2005; 103:1195-1200.
99. Maki R G, Kraft A S, Scheu K, Yamada J, Wadler S, Antonescu C R, Wright J J, Schwartz G K. A Multicenter phase II study of bortezomib in recurrent or metastatic sarcomas. Cancer 2005; 103:1431-1438.
100. O'Connor O A, Wright J, Moskowitz C, Muzzy J, MacGregor-Cortelli B, Stubblefield M, Straus D, Portlock C, Hamlin P, Choi E, Dumetrescu 0, Esseltine D, et al. Phase II clinical experience with the novel proteasome inhibitor bortezomib in patients with indolent non-Hodgkin's lymphoma and mantle cell lymphoma. Journal of Clinical Oncology 2005; 23:676-684.
101. Rajkumar S V, Richardson P G, Hideshima T, Anderson K C. Proteasome inhibition as a novel therapeutic target in human cancer. Journal of Clinical Oncology 2005; 23:630-639.
102. Lashinger L M, Zhu K, Williams S A, Shrader M, Dinney CPN, McConkey D J. Bortezomib abolishes tumor necrosis factor-related apoptosis-inducing ligand resistance via a p21-dependent mechanism in human bladder and prostate cancer cells. Cancer Research 2005; 65:4902-4908.
103. Markovic S N, Geyer S M, Dawkins F, Sharfman W, Albertini M, Maples W, Fracasso P M, Fitch T, LoRusso P, Adjei A A, Erlichman C. A phase II study of bortezomib in the treatment of metastatic malignant melanoma. Cancer 2005; 103:2584-2589.
104. Fernandez Y, Verhaegen M, Miller T P, Rush J L, Steiner P, Opipari A W, Lowe S W, Soengas M S. Differential regulation of noxa in normal Melanocytes and melanoma cells by proteasome inhibition: Therapeutic implications. Cancer Research 2005; 65:6294-6304.
105. Mackay H, Hedley D, Major P, Townsley C, Mackenzie M, Vincent M, Degendorfer P, Tsao M S, Nicklee T, Birle D, Wright J, Siu L, et al. A phase II trial with pharmacodynamic endpoints of the proteasome inhibitor bortezomib in patients with metastatic colorectal cancer. Clinical Cancer Research 2005; 11:5526-5533.

106. Qin J Z, Ziffra J, Stennett L, Bodner B, Bonish B K, Chaturvedi V, Bennett F, Pollock P M, Trent J M, Hendrix M J C, Rizzo P, Miele L, et al. Proteasome inhibitors trigger NOXA-mediated apoptosis in melanoma and myeloma cells. Cancer Research 2005; 65:6282-6293.
107. Berenson J R, Jagannath S, Barlogie B, Siegel D T, Alexanian R, Richardson P G, Irwin D, Alsina M, Rajkumar S V, Srkalovic G, Singhal S, Limentani S, et al. Safety of prolonged therapy with bortezomib in relapsed or refractory multiple myeloma. Cancer 2005; 104:2141-2148.
108. Jeremias I, Kupatt C, Baumann B, Herr I, Wirth T, Debatin K M. Inhibition of nuclear factor kappa B activation attenuates apoptosis resistance in lymphoid cells. Blood 1998; 91:4624-4631.
109. Adams J. Proteasome inhibition in cancer: Development of PS-341. Seminars In Oncology 2001; 28:613-619.
110. Adams J. Development of the proteasome inhibitor PS-341. Oncologist 2002; 7:9-16.
111. Meirow D, Nugent D. The effects of radiotherapy and chemotherapy on female reproduction. Human Reproduction Update 2001; 7:535-543.
112. Gonfloni S, Di Tella L, Caldarola S, Cannata S M, Klinger F G, Di Bartolomeo C, Mattei M, Candi E, De Felici M, Melino G, Cesareni G. Inhibition of the c-Abl-TAp63 pathway protects mouse oocytes from chemotherapy-induced death. Nature Medicine 2009; 15:1179-1185.
113. Kerr J B, Hutt K J, Cook M, Speed T P, Strasser A, Findlay J K, Scott C L. Cisplatin-induced primordial follicle oocyte killing and loss of fertility are not prevented by imatinib. Nature Medicine 2012; 18:1170-1172.
114. Borovskaya T G, Goldberg V E, Fomina T I, Pakhomova A V, Kseneva S I, Poluektova M E, Goldberg E D. Morphological and functional state of rat ovaries in early and late periods after administration of platinum cytostatics. Bulletin of Experimental Biology and Medicine 2004; 137: 331-335.
115. Yucebilgin M S, Terek M C, Ozsaran A, Akercan F, Zekioglu O, Isik E, Erhan Y. Effect of chemotherapy on primordial follicular reserve of rat: An animal model of premature ovarian failure and infertility. Australian & New Zealand Journal of Obstetrics & Gynaecology 2004; 44:6-9.
116. Yeh J, Kim B, Liang Y J, Peresie J. Mullerian inhibiting substance as a novel biomarker of cisplatin-induced ovarian damage. Biochemical and Biophysical Research Communications 2006; 348:337-344.
117. Liu L, Yang C, Herzog C, Seth R, Kaushal G P. Proteasome inhibitors prevent cisplatin-induced mitochondrial release of apoptosis-inducing factor and markedly ameliorate cisplatin nephrotoxicity. Biochemical Pharmacology 2010; 79:137-146.
118. Bae J, Leo C P, Hsu S Y, Hsueh A J W. MCL-1S, a splicing variant of the antiapoptotic BCL-2 family member MCL-1, encodes a proapoptotic protein possessing only the B H3 domain. Journal of Biological Chemistry 2000; 275:25255-25261.
119. Hartley P S, Bayne R A L, Robinson L L L, Fulton N, Anderson R A. Developmental changes in expression of myeloid cell leukemia-1 in human germ cells during oogenesis and early folliculogenesis. Journal of Clinical Endocrinology & Metabolism 2002; 87:3417-3427.
120. Hsu S Y, Hsueh A J W. Tissue-specific Bcl-2 protein partners in apoptosis: An ovarian paradigm. Physiological Reviews 2000; 80:593-614.
121. Hsu S Y, Kaipia A, McGee E, Lomeli M, Hsueh A J W. Bok is a pro-apoptotic Bcl-2 protein with restricted expression in reproductive tissues and heterodimerizes with selective anti-apoptotic Bcl-2 family members. Proceedings of the National Academy of Sciences of the United States of America 1997; 94:12401-12406.
122. Leo C P, Hsu S Y, Chun S Y, Bae H W, Hsueh A J W. Characterization of the antiapoptotic Bcl-2 family member myeloid cell leukemia-1 (Mcl-1) and the stimulation of its message by gonadotropins in the rat ovary. Endocrinology 1999; 140:5469-5477.
123. Flaws J A, Abbud R, Mann R J, Nilson J H, Hirshfield A N. Chronically elevated luteinizing hormone depletes primordial follicles in the mouse ovary. Biology of Reproduction 1997; 57:1233-1237.
124. Kirchmeier M J, Ishida T, Chevrette J, Allen T M. Correlations between the rate of intracellular release of endocytosed liposomal doxorubicin and cytotoxicity as determined by a new assay. Journal Of Liposome Research 2001; 11:15-29.
125. Bagchi, A., E. J. Woods, and J. K. Critser, Cryopreservation and vitrification: recent advances in fertility preservation technologies. Expert review of medical devices, 2008. 5(3): p. 359-70.
126. Bromer, J. G. and P. Patrizio, Fertility Preservation: The Rationale for Cryopreservation of the Whole Ovary. Seminars In Reproductive Medicine, 2009. 27(6): p. 465-471.
127. Cao, Y.-X. and R.-C. Chian, Fertility preservation with immature and in vitro matured oocytes. Seminars in reproductive medicine, 2009. 27(6): p. 456-64.
128. Donnez, J., Advances in fertility preservation for children and adolescents with cancer. European Journal of Cancer, 2009. 45 Suppl 1: p. 418.
129. Ata, B., et al., Cryopreservation of oocytes and embryos for fertility preservation for female cancer patients. Best practice & research Clinical obstetrics & gynaecology, 2010. 24(1): p. 101-12.
130. Practice Committees of American Society for Reproductive, M. and T. Society for Assisted Reproductive, Mature oocyte cryopreservation: a guideline. Feral Steril, 2013. 99(1): p. 37-43.

References Cited in Example 2

1. Woodruff T K (2010) The Oncofertility Consortium-addressing fertility in young people with cancer. *Nature Reviews Clinical Oncology* 7: 466-475
2. Hewitt M, Breen N, Devesa S (1999) Cancer prevalence and survivorship issues: Analyses of the 1992 National Health Interview Survey. *Journal of the National Cancer Institute* 91: 1480-1486
3. Chow W H, Dong L M, Devesa S S (2010) Epidemiology and risk factors for kidney cancer. *Nature reviews Urology* 7: 245-257
4. Smith M A, Freidlin B, Ries L A, Simon R (1998) Trends in reported incidence of primary malignant brain tumors in children in the United States. *Journal of the National Cancer Institute* 90: 1269-1277
5. Society A C (2011) Cancer Facts and Figures 2011. http://wwwcancergov/cancertopics/factsheet/Sites-Types/childhood
6. Gewirtz D A (1999) A critical evaluation of the mechanisms of action proposed for the antitumor effects of the anthracycline antibiotics Adriamycin and daunorubicin. *Biochemical Pharmacology* 57: 727-741
7. Hasinoff B B, Schroeder P E, Patel D (2003) The metabolites of the cardioprotective drug dexrazoxane do not protect myocytes from doxorubicin-induced cytotoxicity. *Molecular Pharmacology* 64: 670-678
8. Swift L M, Sarvazyan N (2000) Localization of dichlorofluorescin in cardiac myocytes: implications for assessment of oxidative stress. *American Journal of Physiology-Heart and Circulatory Physiology* 278: H982-H990
9. Roti Roti E C, Salih S M (2012) Dexrazoxane ameliorates doxorubicin-induced injury in mouse ovarian cells. *Biology of Reproduction* 86: 1-11
10. Kujjo L L, Chang E A, Pereira R J G, Dhar S, Marrero-Rosado B, Sengupta S, Wang H B, Cibelli J B, Perez G I (2011) Chemotherapy-Induced Late Transgenerational Effects in Mice. *Plos One* 6: e17877.
11. Kerr J B et al (2012) The primordial follicle reserve is not renewed after chemical or gamma-irradiation mediated depletion. *Reproduction* 143: 469-476
12. Ben-Aharon I, Bar-Joseph H, Tzarfaty G, Kuchinsky L, Rizel S, Stemmer S M, Shalgi R (2010) Doxorubicin-induced ovarian toxicity. *Reproductive Biology And Endocrinology* 8:20
13. Roti Roti E C, Leisman S K, Abbott D H, Salih S M (2012) Acute Doxorubicin Insult in the Mouse Ovary Is Cell- and Follicle-Type Dependent. *Plos One* 7:
14. Kiyomiya K, Matsuo S, Kurebe M (2001) Mechanism of specific nuclear transport of adriamycin: The mode of nuclear translocation of adriamycin-proteasome complex. *Cancer Research* 61: 2467-2471
15. Baumeister W, Walz J, Zuhl F, Seemuller E (1998) The proteasome: paradigm of a self-compartmentalizing protease. *Cell* 92: 367-380
16. Nederlof P M, Wang H R, Baumeister W (1995) Nuclear localization signals of human and Thermoplasma proteasomal alpha subunits are functional in vitro. *Proceedings of the National Academy of Sciences of the United States of America* 92: 12060-12064
17. Kiyomiya K, Matsuo S, Kurebe M (1998) Proteasome is a carrier to translocate doxorubicin from cytoplasm into nucleus. *Life Sciences* 62: 1853-1860
18. Lyu Y L, Kerrigan J E, Lin C P, Azarova A M, Tsai Y C, Ban Y, Liu L F (2007) Topoisomerase II beta-Mediated DNA double-strand breaks: Implications in doxorubicin cardiotoxicity and prevention by dexrazoxane. *Cancer Research* 67: 8839-8846
19. Adams J (2001) Proteasome inhibition in cancer: Development of PS-341. *Seminars In Oncology* 28: 613-619
20. Amiri K I, Horton L W, LaFleur B J, Sosman J A, Richmond A (2004) Augmenting chemosensitivity of malignant melanoma tumors via proteasome inhibition: Implication for bortezomib (VELCADE, PS-341) as a therapeutic agent for malignant melanoma. *Cancer Research* 64: 4912-4918
21. Huang H B et at (2012) HDAC Inhibitor L-Carnitine and Proteasome Inhibitor Bortezomib Synergistically Exert Anti-Tumor Activity In Vitro and In Vivo. *Plos One* 7:
22. Jeremias I, Kupatt C, Baumann B, Herr I, Wirth T, Debatin K M (1998) Inhibition of nuclear factor kappa B activation attenuates apoptosis resistance in lymphoid cells. *Blood* 91: 4624-4631
23. Flaws J A, Abbud R, Mann R J, Nilson J H, Hirshfield A N (1997) Chronically elevated luteinizing hormone depletes primordial follicles in the mouse ovary. *Biology of Reproduction* 57: 1233-1237
24. Zelinski M B et at (2011) In vivo delivery of FTY720 prevents radiation-induced ovarian failure and infertility in adult female nonhuman primates. *Fertility and Sterility* 95: 1440-U1289
25. Kim S Y, Cordeiro M H, Serna V A, Ebbert K, Butler L M, Sinha S, Mills A A, Woodruff T K, Kurita T (2013) Rescue of platinum-damaged oocytes from programmed cell death through inactivation of the p53 family signaling network. *Cell Death and Differentiation* 20: 987-997

We claim:
1. A method of reducing damage to the ovary of a subject receiving chemotherapy, comprising the step of
   (a) administering to the subject an amount of a proteasome inhibitor effective to reduce damage to the subject's ovary within a therapeutic time window prior to administration of a chemotherapeutic agent.
2. The method of claim 1, wherein the time window is in the range of about 30 minutes to about 2 hours.
3. The method of claim 2, wherein the time window is about 30 minutes.
4. The method of claim 2, wherein the time window is about 45 minutes.
5. The method of claim 2, wherein the time window is about one hour.
6. The method of claim 2, wherein the time window is about 1.5 hours.
7. The method of claim 2, wherein the time window is about two hours.
8. The method of claim 1, wherein the proteasome inhibitor is administered at a dose in the range of 3% to 99% of the dose of the proteasome inhibitor typically used in a chemotherapy regimen.
9. The method of claim 8, wherein the dose is 33% of the dose typically used in a chemotherapy regimen.
10. The method of claim 1, wherein the dose is in the range of about 0.04 mg/m$^2$ to about 1 mg/m$^2$.
11. The method of claim 10, wherein the dose is about 0.43 mg/m$^2$.
12. The method of claim 1, wherein the proteasome inhibitor is selected from the group consisting of bortezomib, carfilzomib, marizomib, CEP-18770, MLN-9708. ONX-0912, MG-132, PR-171, peptide vinyl sulfone, peptide 2-keto-1,3, 4-oxadiazole, NPI-0052, TMC-95A, CVT-650, 2-aminobezylstatine derivative, trimethol-L-phenylalanine tripeptide, thiostrepton, MG-162, and mixtures thereof.
13. The method of claim 12, wherein the proteasome inhibitor is bortezomib.
14. The method of claim 12, wherein the proteasome inhibitor is MG-132.
15. The method of claim 1, wherein the chemotherapeutic agent is selected from the group consisting of anthracyclines, platinum drugs, intercalating chemotherapeutic agents, topoisomerase poisons, cyclophosphamide drugs, and mixtures thereof.
16. The method of claim 15, wherein the anthracycline is selected from the group consisting of Daunorubicin (Daunomycin), Daunorubicin (liposomal), Doxorubicin (Adriamycin), Doxorubicin (liposomal i.e. Doxil), Epirubicin, Idarubicin, Valrubicin, Mitoxantrone, and mixtures thereof.
17. The method of claim 16, wherein the anthracycline is Doxorubicin.
18. The method of claim 15, wherein the platinum drug is selected from the group consisting of Cisplatin, Carboplatin, Oxaliplatin, and mixtures thereof.
19. The method of claim 15, wherein the intercalating chemotherapeutic agent is selected from the group consisting of dactinomycin, erlotinib, and mixtures thereof.

20. The method of claim 15, wherein the topoisomerase poison is selected from the group consisting of etoposide (VP-16), teniposide, doxorubicin, daunorubicin, mitoxantrone, amsacrine, ellipticines, aurintricarboxylic acid, HU-331, irinotecan, topotecan, camptothecin, lamellarin D, and mixtures thereof.

21. The method of claim 15, wherein the cyclophosphamide drug is selected from cyclophosphamide, alkylating chemotherapeutic agents, ifosfamide, melphalan, budulfan, uracil mustard, chlorambucil, and mixtures thereof.

* * * * *